(12) United States Patent
Farkash et al.

(10) Patent No.: US 12,033,742 B2
(45) Date of Patent: Jul. 9, 2024

(54) NONINVASIVE MULTIMODAL ORAL ASSESSMENT AND DISEASE DIAGNOSES APPARATUS AND METHOD

(71) Applicant: Align Technology, Inc., San Jose, CA (US)

(72) Inventors: Shai Farkash, Hod HaSharon (IL); Yossef Atiya, Modin-Maccabim-Reut (IL); Maayan Moshe, Ramat HaSharon (IL); Moti Ben-Dov, Tel Mond (IL); Raphael Levy, Jerusalem (IL); Doron Malka, Tel Aviv (IL)

(73) Assignee: Align Technology, Inc., San Jose, CA (US)

( * ) Notice: Subject to any disclaimer, the term of this patent is extended or adjusted under 35 U.S.C. 154(b) by 285 days.

(21) Appl. No.: 17/549,830

(22) Filed: Dec. 13, 2021

(65) Prior Publication Data

US 2022/0189611 A1 Jun. 16, 2022

Related U.S. Application Data

(60) Provisional application No. 63/124,712, filed on Dec. 11, 2020.

(51) Int. Cl.
| | |
|---|---|
| *G06T 7/00* | (2017.01) |
| *A61B 1/04* | (2006.01) |
| *A61B 1/06* | (2006.01) |
| *A61B 1/24* | (2006.01) |
| *A61C 9/00* | (2006.01) |

(Continued)

(52) U.S. Cl.
CPC ............ *G16H 30/40* (2018.01); *A61B 1/043* (2013.01); *A61B 1/0638* (2013.01); *A61B 1/24* (2013.01); *A61C 9/0053* (2013.01); *G06T 7/0016* (2013.01); *G16H 50/20* (2018.01); *G16H 70/60* (2018.01); *G06N 20/00* (2019.01); *G06T 2200/04* (2013.01); *G06T 2207/10024* (2013.01); *G06T 2207/10048* (2013.01); *G06T 2207/10064* (2013.01); *G06T 2207/20081* (2013.01); *G06T 2207/30036* (2013.01); *G06T 2207/30096* (2013.01)

(58) Field of Classification Search
None
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |

(Continued)

*Primary Examiner* — Sultana M Zalalee
(74) *Attorney, Agent, or Firm* — Shay Glenn LLP

(57) ABSTRACT

Methods and apparatuses for assessing oral health and automatically providing diagnosis of one or more oral diseases. Described herein are intraoral scanning methods and apparatuses for collecting and analyzing image data and to detect and visualize features within image data that are indicative of oral diseases or conditions, such as gingival inflammation or oral cancer. These methods and apparatuses may be used for identifying and evaluating lesions, redness and inflammation in soft tissue and caries and cracks in the teeth. The methods can include training a machine learning model and using the trained machine learning model to provide a diagnosis of an oral disease or condition based on image data collected using multiple scanning modes of an intraoral scanner.

21 Claims, 33 Drawing Sheets

(51) Int. Cl.
*G16H 30/40* (2018.01)
*G16H 50/20* (2018.01)
*G16H 70/60* (2018.01)
*G06N 20/00* (2019.01)

(56) References Cited

U.S. PATENT DOCUMENTS

| | | |
|---|---|---|
| 6,334,853 B1 | 1/2002 | Kopelman et al. |
| 6,463,344 B1 | 10/2002 | Pavloskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,136,972 B2 | 11/2018 | Sabina et al. |
| 10,380,212 B2 | 8/2019 | Elbaz et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,699,163 B1 * | 6/2020 | Shah .................. G06F 18/214 |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Ariel et al. |
| 11,096,765 B2 | 8/2021 | Yossef et al. |
| 11,238,586 B2 | 2/2022 | Mikhail et al. |
| 2019/0029784 A1 | 1/2019 | Moalem et al. |
| 2019/0231492 A1 * | 8/2019 | Sabina ................ A61B 1/0646 |
| 2019/0388193 A1 | 12/2019 | Ofer et al. |
| 2020/0281700 A1 | 9/2020 | Avi et al. |
| 2020/0281702 A1 | 9/2020 | Avi et al. |
| 2020/0315434 A1 | 10/2020 | Kopelman et al. |
| 2020/0349705 A1 | 11/2020 | Mikhail et al. |
| 2020/0364860 A1 * | 11/2020 | Kearney ................ G16H 30/40 |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |
| 2021/0275028 A1 * | 9/2021 | Kumar ................ A61B 5/4552 |
| 2023/0222767 A1 * | 7/2023 | Ertl .................... G06V 10/764 |
| | | 600/408 |

* cited by examiner

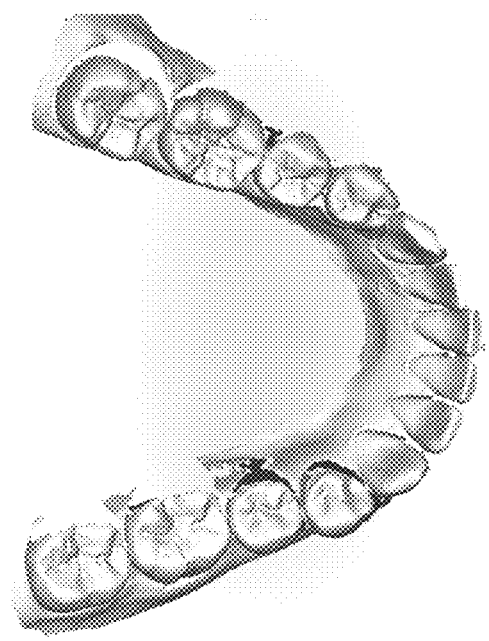
FIG. 11A
FIG. 11C
FIG. 11B

NONINVASIVE MULTIMODAL ORAL ASSESSMENT AND DISEASE DIAGNOSES APPARATUS AND METHOD

CLAIM OF PRIORITY

This patent application claims priority to U.S. Provisional Patent Application No. 63/124,712, titled "NONINVASIVE MULTIMODAL ORAL ASSESSMENT AND DISEASE DIAGNOSES APPARATUS AND METHOD," filed on Dec. 11, 2020, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may relate to oral scanners and methods of their use, and particularly for generating three-dimensional (3D) representations of the teeth and gingiva and other soft tissues of the mouth. In particular, described herein are methods and apparatuses that may be useful in scanning, including 3D scanning, and analyzing the intraoral cavity for detection, diagnosis, treatment, and longitudinal tracking of oral conditions.

BACKGROUND

According to the World Health Organization, oral diseases are major public health problems due to their high incidence and prevalence across the globe. Oral diseases can affect not only the teeth but also soft tissue, ligaments and bone that support the teeth (periodontium). Periodontal disease is widely regarded as the second most common dental disease worldwide, after dental decay, and is estimated to affect 20-50% of the global population. Periodontitis has been linked to increased inflammation in the body and is associated with an increased risk of other medical conditions, such as stroke, myocardial infarction, atherosclerosis, hypertension, and memory problems. Currently, diagnosis of periodontal disease is primarily based on invasive clinical observations and x-rays radiographs. Conventional diagnosis is typically done by visually inspecting the gum tissue around and taking measurements around each tooth to measure the extent of periodontal ligament fiber loss around each tooth using a probe. This process is time consuming and is invasive, which can cause further irritation to the gums. In addition, probe measurements do not provide information related to other aspects of a patient's oral condition that may be related to or contribute to periodontal disease. Current noninvasive techniques such as optical coherence tomography (OCT), near-infrared (NIR) spectroscopy, photoacoustic and conventional fluorescence imaging each has its limitations, such as the need for contrast agent, bulkiness, high ownership price and other factors.

The prevalence of oral and throat cancer is estimated to be about 480,000 new cases per year worldwide. Dentists routinely conduct visual and tactile examinations for oral and oropharyngeal cancer in patients. In a typical oral cancer screening exam, a dentist or other specialist inspects the inside of the patient's mouth to check for red or white patches or mouth sores. The dentist or specialist additionally typically feels the tissues inside the mouth to check for lumps or other abnormalities. In some cases, dye is used to improve the visibility of lesions during visual exam. However, conventional examination and screening procedures for oral cancer may be subjective and inconsistent and may only be able to detect cancer after developing to a moderate to severe stage.

It would be beneficial to provide tools that may aid in the inspection, visualization, and analysis regarding the health of a patient's oral health, including soft tissue around the teeth. It would also be beneficial to provide one or more tools that may aid in monitoring the health of the patient's periodontium and teeth over time for early detection or prevention of periodontal disease, cancer, and other oral diseases.

SUMMARY

The apparatuses (e.g., devices, systems, etc.) and methods described herein solve the above-described problems by providing improved techniques for evaluating a subject's oral health and visualizing and screening individuals for early detection of oral conditions, resulting in improved outcomes. The apparatuses and methods can include determining the health of a subject's periodontium and teeth based on images collected from one or more oral scan using an intraoral scanner. The methods and apparatuses can be configured to analyze scans having information about both external and internal structures of a subject's dentition and periodontium. These methods and apparatuses may generate a three-dimensional (3D) model of a subject's gums and teeth that includes both surface topography and internal structures of the teeth (e.g., roots, dentin, dental fillings, cracks and/or caries) and the periodontium (e.g., gingiva, periodontal ligament, cementum and/or alveolar bone).

The intraoral scanning systems may be capable of collecting images of the subject's oral cavity using multiple imaging modalities, including 3D volumetric imaging, color imaging, infrared (e.g., near infrared (NIR)) imaging, color imaging spectroscopy, and/or NIR spectroscopy. In some variations, the intraoral scanning apparatuses may include aspects of one or more iTero oral scanning systems (e.g., iTero 5D) manufactured and sold by Align Technology, Inc. headquartered in San Jose, California, U.S.A. Various features and methods of using such intraoral scanning apparatuses are described, for example, in U.S. Pat. Nos. 10,123,706 and 10,390,913, each of which is herein incorporated by reference in its entirety.

The information collected using the different modalities of the intraoral scanner can be used to provide information related to different aspects of the periodontium. For example, 3D volumetric data can be used to determine whether there is gum recession, 2D color image data can be used to determine whether the gums are inflamed, NIR image data can be used to determine whether there is gum recession or bone loss, and/or NIR spectroscopy data can be used to determine whether blood measurements indicate inflammation. These different types of data can be combined to provide a more comprehensive picture of the health of the periodontium and teeth.

In some examples, the apparatuses and methods include fluorescence imaging in conjunction with other imaging modalities (e.g., 3D volumetric imaging, color imaging, infrared NIR imaging and/or NIR spectroscopy) to provide a more comprehensive assessment of the subject's oral condition. Fluorescence imaging may be used to provide information related to health of soft tissues of the mouth and be used to detect precancerous or cancerous lesions. Thus, in addition to detecting tooth conditions (e.g., cavities, cracks, etc.) and gingival conditions (e.g., mild, moderate or severe gingival inflammation, etc.) using other imaging modalities (e.g., volumetric, color, NIR), fluorescence imaging can be used to detect cancerous and/or precancerous lesions in the soft tissues around the teeth. Further, when combined with information provided by the other imaging modalities, the fluorescence imaging data may provide a more accurate and faster diagnosis of oral cancer and precancers.

The methods described herein can provide routinely accessible preventive diagnostics service, thereby improving patient's oral health. In some cases, a single intraoral scanner can be used to track a patient's oral health and/or provide a quantitative assessment of intraoral lesions. In some cases, the intraoral scanning is done substantially without X-ray radiation, thereby reducing the patent's exposure to such radiation.

The apparatuses and methods can be used to monitor the health of the patient's periodontium and teeth over time, thereby allowing early detection or prevention of periodontal and other oral diseases. In some variations, images of the patient's mouth are collected at different times and compared with each other to track the progress of an oral treatment. Changes over time may be displayed in time lapse to present the changes to the user in a condensed time frame.

Any of the apparatuses and/or methods can implement machine learning techniques and classification models to automatically assess and/or diagnose periodontal or dental conditions. Examples of machine learning systems that may be used include, but are not limited to, Convolutional Neural Networks (CNN), Decision Tree, Random Forest, Logistic Regression, Support Vector Machine, AdaBoosT, K-Nearest Neighbor (KNN), Quadratic Discriminant Analysis, Neural Network, etc. The machine learning classification models can be configured to generate an output data set that includes a probability that the data set includes one or more or periodontal and/or dental conditions. In some examples, the machine learning classification model can output a linear scale rating (e.g., a probability between 0.0 to 1.0).

As described in greater detail herein, apparatuses and/or methods described herein may be based on or include collecting a 3D scan of the patient's oral cavity. Collecting the 3D scan may include taking the 3D scan, including scanning the patient's dental arch directly (e.g., using an intraoral scanner), acquiring the 3D scan information from a separate device and/or third party, and/or acquiring the 3D scan from a memory. The 3D scan can be used to generate a 3D mesh of points representing the portions of the patient's oral cavity, such as the patient's teeth and gums. Additional information may be collected with the 3D scan, including patient information (e.g., age, gender, etc.).

The system can be configured to render (e.g., in a display or other output) the different types of tissue (e.g., tooth, periodontium, cancer, precancer, bone and/or plaque) using different colors or combination of colors. The colors may be chosen based on the type and level of risk they represent. The pixel wise imaged oral lesions may be overlaid onto the concurrently captured 3D model using machine learning. Machine learning can also be used to reconstruct the lesion topology by combining several 2D images of the lesion structure capture methods taken at different angles. The data captured by the scanner (e.g., color 3D model combining the topography of the teeth and the lesions mapping) can be maintained in a designated patient database for longitudinal monitoring and preservation of patient's oral health.

Any of the apparatuses and/or methods described herein may be part of an intraoral scanning apparatus or method or may be configured to work with an intraoral scanning apparatus or method.

For example, described herein are methods that include: receiving or accessing data collected from an oral scan of the subject's oral cavity, the data including at least three of: 3D surface data, color image data, near-infrared (NIR) data, and fluorescence imaging data; identifying one or more features indicative of gingival inflammation in the collected data using a trained machine learning model, wherein the trained machine learning model is trained on image data including at least three of: previous 3D surface data, previous color image data, previous near-infrared (NIR) data, and previous fluorescence imaging data, wherein the scan data used to train the machine learning model is filtered based on a threshold angle between images of the image data and a threshold distance between the images of the image data; and outputting an indication of gingival inflammation based on the identified one or more features indicative of gingival inflammation.

Outputting may comprise marking the one or more features indicative of gingival inflammation on images or a 3D model of the subject's dental arch on a display. Marking the one or more features indicative of gingival inflammation may include highlighting or labeling the features indicative of gingival inflammation. The one or more features indicative of gingival inflammation may include one or more measurements of the cementoenamel junction (CEJ) that are sufficiently high to be associated with gum recession. The one or more features indicative of gingival inflammation may include one or more measurements of the gums that that are sufficiently red to be associated with gingival inflammation. The one or more features indicative of gingival inflammation may include one or more measurements of dental pocket depth that are sufficiently high to be associated with gum recession. The one or more features indicative of gingival inflammation may include one or more measurements of blood serum concentration sufficiently high to be associated with gingival inflammation.

In any of these methods, a trained machine learning model is further trained based on X-ray image data, periodontal chart data and visual inspection/tactile data. The trained machine learning model may be further trained based on NIR spectroscopy data.

Any of these methods may further include monitoring changes to the one or more features indicative of gingival inflammation over time to determine improvement or worsening of symptoms of gingival inflammation. For example, the method may include updating the diagnosis of the one or more gingival inflammations based on the changes to the one or more features indicative of gingival inflammation. Any of these methods may include providing a time lapse video showing the changes to the one or more features indicative of gingival inflammation.

For example, a method of diagnosing oral cancer or precancer in a subject may include: capturing data using an intraoral scanner on the subject's oral cavity, wherein the captured data includes 3D surface data, color image data, near-infrared (NIR) data, and fluorescence imaging data; identifying one or more cancer or precancer lesions in the 3D model in the captured data using a trained machine learning model, wherein the trained machine learning model is trained on image data including includes previous 3D surface data, previous color image data, previous near-infrared (NIR) data, and previous fluorescence imaging data, wherein the scan data used to train the machine learning model is filtered based on a threshold angle between images of the image data and a threshold distance between the images of the image data; and outputting an indication of oral cancer or precancer based on the identified one or more cancer or precancer lesions.

Capturing the data may include concurringly collecting the 3D surface data, color image data, near-infrared (NIR) data, and fluorescence imaging data.

Any of these methods may include determining a size and shape of the one or more cancer or precancer lesions.

The trained machine learning model may be further trained based on X-ray image data, periodontal chart data and visual inspection/tactile data. The trained machine learning model may be further trained based on NIR spectroscopy data. The trained machine learning model may be further trained based on fluorescence imaging data collected from previous scans of the subject's oral cavity.

For example, a system may include: one or more processors; a memory, accessible by the one or more processors and storing computer-program instructions, that, when executed by the one or more processors, perform a computer-implemented method comprising: receiving or accessing data collected from an oral scan of the subject's oral cavity, the data including at least three of: 3D surface data, color image data, near-infrared (NIR) data, and fluorescence imaging data; identifying one or more features indicative of gingival inflammation in the collected data using a trained machine learning model, wherein the trained machine learning model is trained on image data including at least three of: previous 3D surface data, previous color image data, previous near-infrared (NIR) data, and previous fluorescence imaging data, wherein the scan data used to train the machine learning model is filtered based on a threshold angle between images of the image data and a threshold distance between the images of the image data; and outputting an indication of gingival inflammation gingival inflammation based on the identified one or more features indicative of gingival inflammation.

Any of these systems may include a hand-held wand having at least one image sensor and a plurality of light sources, wherein the plurality of light sources may be configured to emit light at a visible light range, a florescent light range, and an infrared light range.

The computer-implemented methods described herein may further comprise: capturing data of at least a portion of the subject's teeth as the intraoral scanner is moved over the teeth, wherein the captured data includes 3D surface data, color image data, near-infrared (NIR) data, and fluorescence imaging data.

The apparatuses (e.g., systems and devices) and methods and/or nay of the features described herein, alone or in combination, may be used with any of the systems and methods, including (but not limited to) intraoral scanners and methods of using them, described in one or more of U.S. Pat. No. 10,123,706, patented on Nov. 13, 2018, and entitled "INTRAORAL SCANNER WITH DENTAL DIAGNOSTICS CAPABILITIES," U.S. Pat. No. 10,390,913, patented on Aug. 27, 2019, entitled "DIAGNOSTIC INTRAORAL SCANNING," and U.S. Provisional Patent Application No. 62/955,968, entitled "MACHINE LEARNING DENTAL SEGMENTATION SYSTEM AND METHODS USING SPARSE VOXEL REPRESENTATIONS," each of which are herein incorporated by reference in their entirety.

A "patient," as used herein, may be any subject (e.g., human, non-human, adult, child, etc.) and may be alternatively and equivalently referred to herein as a "patient" or a "subject." A "patient," as used herein, may but need not be a medical patient. A "patient," as used herein, may include a person who receives an oral examination or treatment, including one or more evaluations for periodontal, dental, or other oral conditions.

These and other aspects, details and advantages are described herein.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

FIGS. 11A-11C illustrate images taken using different modalities of an intraoral scanner: FIG. 11A shows an example 3D surface scan; FIG. 11B shows an example image with internal structures of a tooth taken using penetrative (NIR) illumination; and FIG. 11C shows an example image of the tooth taken using color light.

FIG. 12A illustrates a high-level diagram of the machine learning architecture; FIG. 12B illustrates anonymization pipeline components; and FIG. 12C illustrates data processing and machine learning components.

FIG. 13A illustrates a component diagram; FIG. 13B illustrates a diagram for main components and data flow for entry point; FIG. 13C illustrates a diagram for main components and data flow for getting labelers tasks; FIG. 13D illustrates a flow diagram for main components and data flow for authorization flow; FIG. 13D illustrates a flow diagram for main components and data flow for getting task data; and FIG. 13E illustrates a flow diagram for main components and data flow for updating task labeling data.

FIG. 14A shows the internal structure (NIR) images and color images without labels; and FIG. 14B shows the images of FIG. 14A with features identified as being dental caries labeled.

DETAILED DESCRIPTION

Described herein are apparatuses (e.g., systems, computing device readable media, devices, etc.) and methods for analyzing and processing image scans of a subject's oral cavity. The apparatuses and methods can combine images taken using multiple imaging modalities (e.g., using different wavelength ranges of illumination light and/or measuring different wavelength ranges of reflected or emitted light) to form a 3D model. The apparatuses and methods can use machine learning to compare data from one oral scan to other oral scans to identify features with the images that are indicative of one or more oral diseases or conditions, and provide a probable diagnosis of one or more oral diseases or conditions.

Figure 1B:
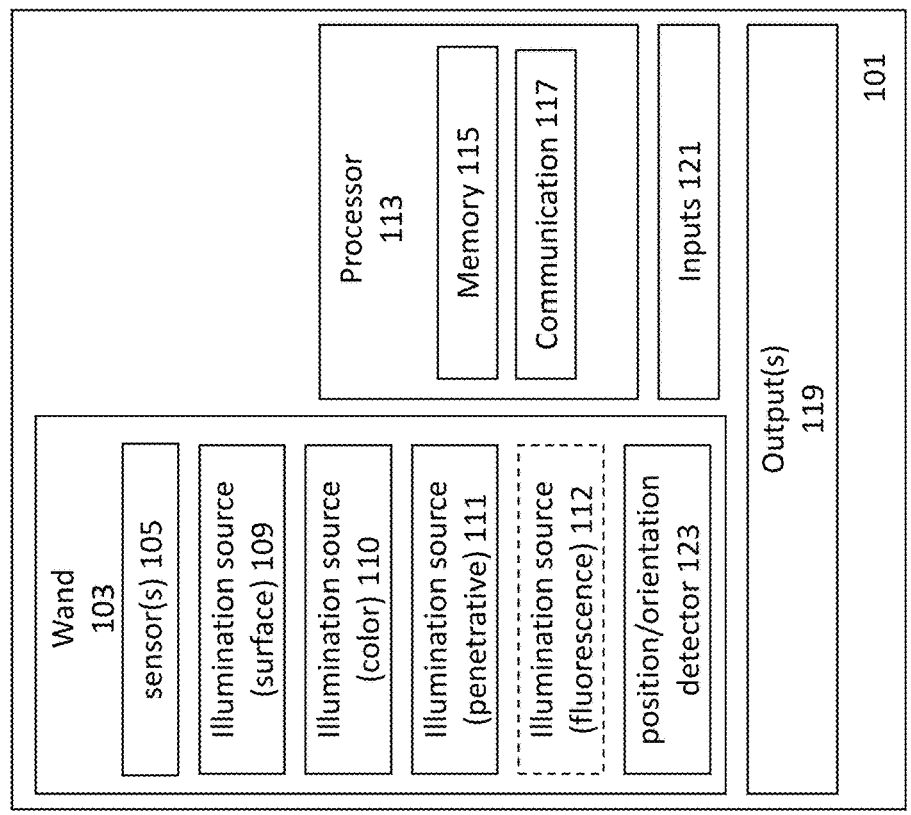
FIG. 1B schematically illustrates an example of an intraoral scanner configured to generate a model of subject's teeth having both surface and internal features.
Figure 1A:
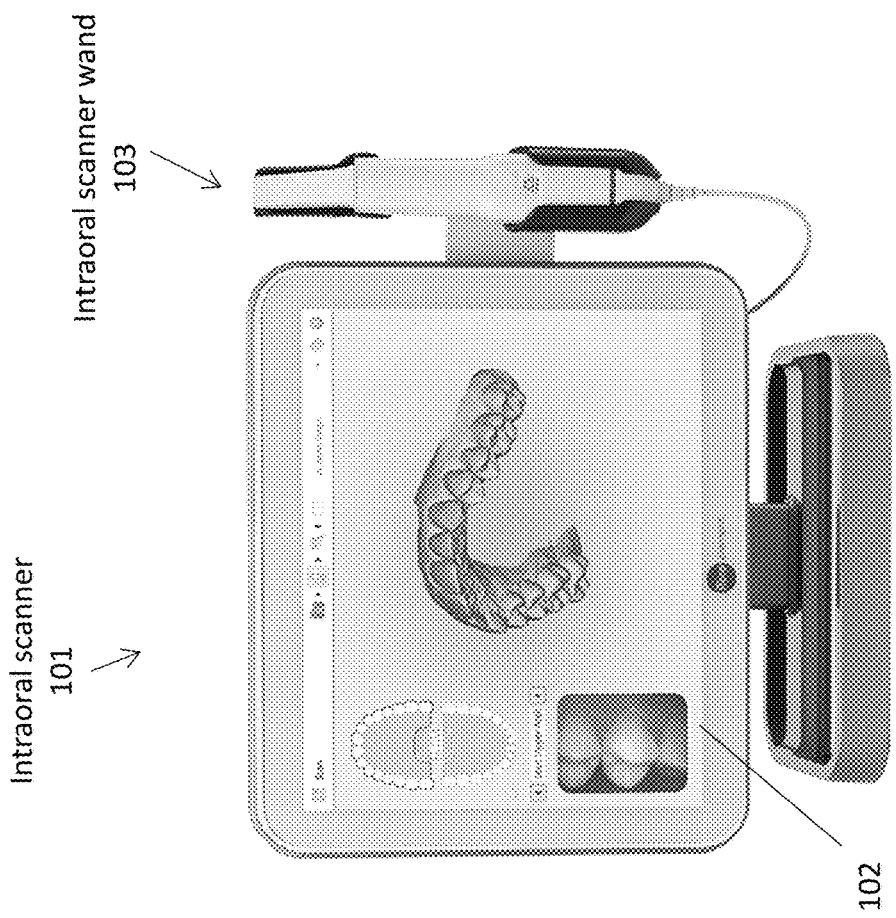
FIG. 1A illustrates one example of a 3D (color) intraoral scanner that may be adapted for used as described herein to generate a model of subject's teeth having both surface and internal features.

FIGS. 1A-1B show an example intraoral scanning system 101 for generating images of a subject's intraoral region (e.g., tooth or teeth, gums, jaw, etc.) which may include surface features and internal features of the teeth, gums and/or bone. In FIG. 1A the exemplary intraoral scanner 101 may include an intraoral scanner wand 103 and be configured or adapted to generate images having both surface and internal features, or just internal (penetrative) scans on a display 102. Although in many instances surface scanning (including color scans) may be helpful and useful, the penetrative (IR) scanning may, in some of the variations described herein, be sufficient. In some variations, the scanner 101 may additionally be configured for fluorescence imaging, data from which may be combined with images collected using other modalities.

As shown schematically in FIG. 1B, the exemplary intraoral scanner may include a handle or wand 103 that can be hand-held by an operator (e.g., dentist, dental hygienist, technician, etc.) and moved over a subject's teeth, gums and/or bone to scan both surface and internal structures. The wand may include one or more sensors 105 (e.g., cameras such as CMOS, CCDs, detectors, etc.) and one or more light sources 109, 110, 111, 112. In FIG. 1B, four light sources are shown: a first light source 109 configured to emit light in a first spectral range for detection of surface features (e.g., visible light, monochromatic visible light, or non-visible light); a second (color) light source 110 (e.g., white light between 400-700 nm, e.g., approximately 400-600 nm); a third light source 111 configured to emit light in a second spectral range for detection of internal features within the teeth, gums and/or bone (e.g., by trans-illumination, small-angle penetration imaging, laser florescence, etc., which may generically be referred to as penetration imaging, e.g., in the near-IR); and an optional fourth light source 112 configured to emit light to cause fluorescence emission of one or more structures in the subject's mouth. Although separate illumination sources are shown in FIG. 1B, in some variations a selectable light source may be used. For example, the second color light source 110 may also be used to cause fluorescence emission. The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner, such as a foot petal, keyboard, console, touchscreen, etc.

In general, any appropriate light source(s) may be used based on the type of imaging information being collected. For example, any of these apparatuses may include a visible light source or other (including non-visible) light source for surface detection (e.g., at or around 680 nm, or other appropriate wavelengths). A color light source, typically a visible light source (e.g., "white light" source of light) for color imaging may also be included. In addition, a penetrating light source for penetration imaging (e.g., infrared, such as specifically near infrared light source) may be also be included.

The intraoral scanner 101 may also include one or more processors, including linked processors or remote processors, for both controlling the wand 103 operation, including coordinating the scanning and in reviewing and processing the scanning and generation of a 3D model including surface and internal features. As shown in FIG. 1B the one or more processors 113 may include or may be coupled with a memory 115 for storing scanned data (surface data, internal feature data, etc.). Communications circuitry 117, including wireless or wired communications circuitry may also be included for communicating with components of the system (including the wand) or external components, including external processors. For example, the system may be configured to send and receive scans or 3D models. One or more additional outputs 119 may also be included for outputting or presenting information, including display screens, printers, etc. As mentioned, inputs 121 (buttons, touchscreens, etc.) may be included and the apparatus may allow or request user input for controlling scanning and other operations.

The intraoral scanner 101 can be configured to obtain images based on different imaging modalities. For example, three-dimensional (3D) surface structures (e.g., using a first illumination source 109), two-dimensional (2D) color images (e.g., using a second illumination source 110), and 2D internal structures (e.g., using a third illumination source 111) of the oral cavity can be captured. FIGS. 11A-11C show images collected from three different modalities of an intraoral scanning system. FIG. 11A shows an example 3D surface scan; FIG. 11B shows an example image with internal structures of a tooth taken using penetrative (NIR) illumination; and FIG. 11C shows an example image of the tooth taken using color light. The images can capture various features of the dental arch, including one or more teeth and periodontium (gums, connective tissue, and bone around the teeth). The surface structures images may be obtained by illuminating the oral cavity with visible wavelength of light to obtain color images. The internal structures may be obtained by illuminating the oral cavity using generally penetrative wavelengths of light, such as infrared radiation. In some instances, the infrared illumination includes near infrared radiation (NIR), for example, in the range of 700 to 1090 nm (e.g., 850 nm). Other wavelengths and ranges of wavelengths may be used, including wavelengths shorter than the visible spectrum The intraoral scanner 101 may be effective in combining a 3D surface model of the teeth, gums and/or bone with the imaged internal features such as lesions (caries, cracks, etc.) that may be detected by the use of penetration imaging by using an intraoral scanner that is adapted for separate but concurrent (or nearly-concurrent) detection of both the surface and internal features. Combining surface scanning and the penetration imaging may be performed by alternating or switching between these different modalities in a manner that allows the use of the same coordinate system for the two. Alternatively, both surface and penetrative scanning may be simultaneously viewed, for example, by selectively filtering the wavelengths imaged to separate the IR (e.g., NIR) light from the visible light. The 3D surface data may therefore provide important reference and angle information for the internal structures and may allow the interpretation and analysis of the penetrating images that may otherwise be difficult or impossible to interpret.

The intraoral scanner 101 can be configured to generate a volumetric model, which includes a virtual representation of an object in 3D in which internal regions (structures, etc.) are arranged within the volume in three physical dimensions in proportion and relative to the other internal and surface features of the object which is being modeled. For example, a volumetric representation of the teeth, gums and/or bone may include the outer surface as well as internal structures within the teeth and gums (beneath the surfaces of the teeth and gums) proportionately arranged relative to the teeth, gums and/or bone. The volumetric model can include a combination of 2D color images (surface images) and infrared (e.g., NIR) images captured during one or more scans of the patient's oral cavity. The volumetric model can be that a section in a way that substantially corresponds to a section through the teeth, gums and/or bone, showing position and size of internal structures. A volumetric model may be section from any (e.g., arbitrary) direction and correspond to equivalent sections through the object being modeled. A volumetric model may be electronic or physical. A physical volumetric model may be formed, e.g., by 3D printing and/or using one or more other manufacturing technologies. The volumetric models described herein may extend into the volume completely (e.g., through the entire volume of the teeth, gums and/or bone) or partially (e.g., into the volume being modeled for some minimum depth, e.g., 2 mm, 3 mm, 4 mm, 5 mm, 6 mm, 7 mm, 8 mm, 9 mm, 10 mm, 12 mm, etc.).

In some variations, the NIR capability of the intraoral scanner 101 can be used to provide NIR absorption spectroscopy measurements to determine physiological parameters such as blood sugar and/or oxygen saturation (pulse oximetry).

Oral Assessment and Diagnostics

The intraoral scanning systems described herein can be configured to assess the condition of the patient's oral health based on one or more scans of the patient's mouth, in some instances, a single scan of the patient's mouth. The assessments may be performed using machine learning to combine the images collected using the multiple modalities (e.g., 3D, color images, NIR images, and/or NIR spectroscopy) to recognize indications of gingival inflammation and other symptoms of one or more oral conditions. In addition, analyses may be performed to determine whether the images indicate one or more diseases or conditions and provide a diagnosis based on the indications.

Figure 2:
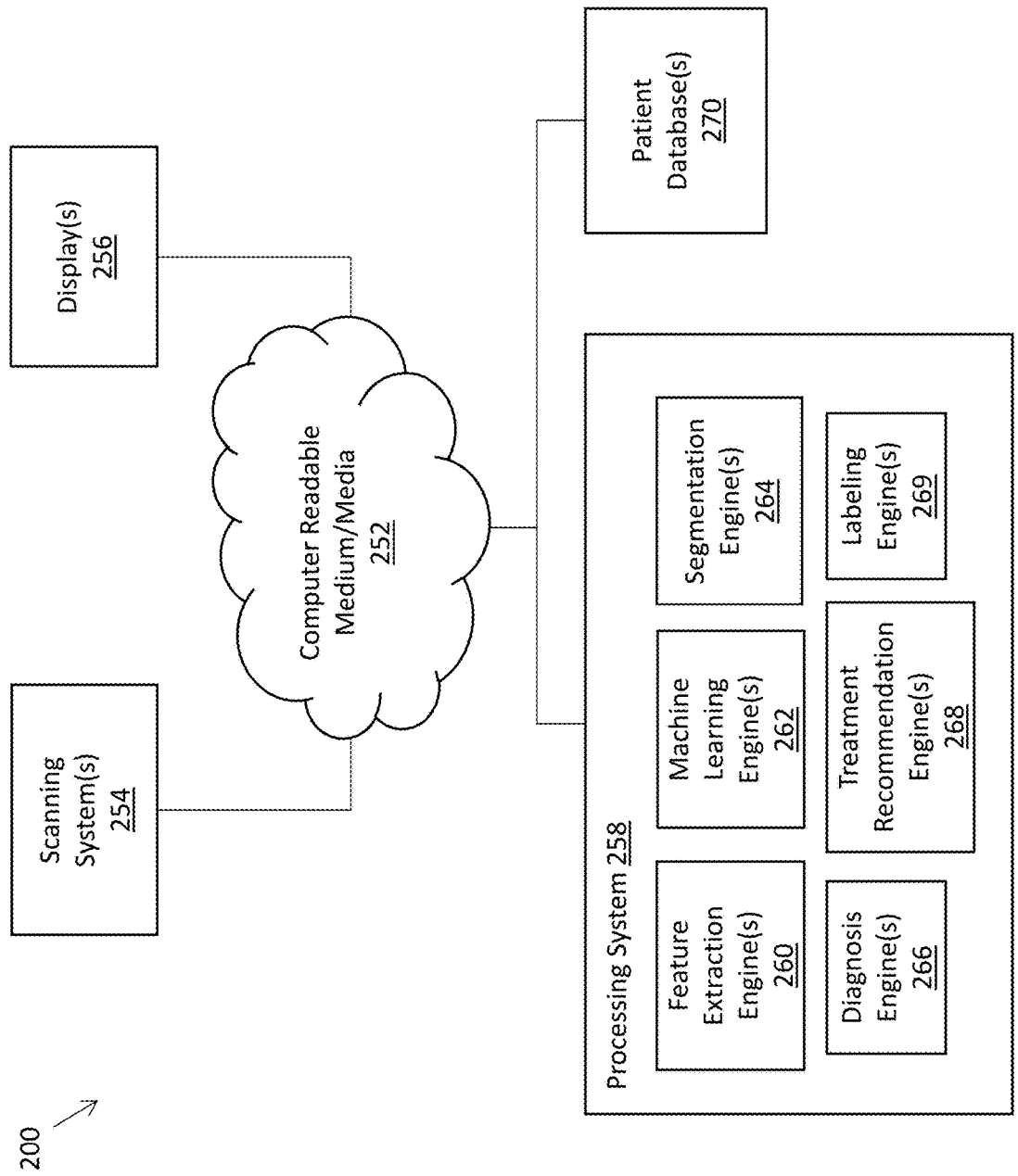
FIG. 2 is a diagram showing an example of a computing environment configured to scan a patient's oral cavity, assess the patient's oral health, monitor a patient's oral health and/or provide a diagnosis of one or more oral conditions.

FIG. 2 is a diagram showing an example of a computing environment 200 configured to facilitate gathering and/or processing digital scans of one or more oral scans, which can be used to perform periodontal assessment and diagnoses analysis. The computing environment 200 can include a computer-readable medium 252, a scanning system 254, a display system 256, a printer(s) 257, a patient database 270, and a processing system 258. One or more of the modules in the computing environment 200 may be coupled to one another or to modules not explicitly shown.

The computer-readable medium 252 and other computer readable media discussed herein are intended to represent a variety of potentially applicable technologies. For example, the computer-readable medium 252 can be used to form a network or part of a network. Where two components are co-located on a device, the computer-readable medium 252 can include a bus or other data conduit or plane. Where a first component is co-located on one device and a second component is located on a different device, the computer-readable medium 252 can include a wireless or wired back-end network or LAN. The computer-readable medium 252 can also encompass a relevant portion of a WAN or other network, if applicable.

The scanning system 254 may include a computer system configured to scan a patient's oral cavity, including the periodontium and/or the teeth. In some instances, the scanning system 254 is configured to scan a dental arch of the patient, which includes at least a portion of a patient's dentition formed by the patient's maxillary and/or mandibular teeth, and which may be viewed from an occlusal perspective. The scanning system 254 may include memory, one or more processors, and/or sensors to detect contours on a patient's dental arch. The scanning system 254 may be implemented as a camera, an intraoral scanner, an x-ray device, an infrared device, fluorescence imaging device, etc. The scanning system 254 may be configured to produce 3D and/or 2D scans of the patient's dental arch. The scanning system 254 may be configured to receive 2D or 3D scan data taken previously or by another system. The display system 256 may include a computer system configured to display at least a portion of the periodontium and/or teeth. The display 256 may be implemented as part of a computer system and/or as a display of a dedicated intraoral scanner.

The processing system 258 may include one or more processors configured to process scan data from the scanning system 254. The processing system 258 may include one or more of: feature extraction engine(s) 260, labeling engine(s) 269, machine learning engine(s) 262, segmentation engine(s) 264, diagnosis engine(s) 266, and treatment recommendation engine(s) 268. The feature extraction engine(s) 262 may extract features from the oral scan data. The extracted features can be used as input by the machine learning engine 264 to train a machine learning model. In some cases, a labeling engine 262 is used to label the different features related to one or more diseases or conditions. The machine learning engine 264 may train the machine learning model based upon patient data from, for example, a patient database 270, which can include historical patient data, patient demographics, tooth measurements, tooth surface mesh, processed tooth features, and/or other patient information. The patient database 270 may be part of a computing device which includes the processing system 258 or may be part of a separate computing device.

The machine learning model may be trained based on any of a number of data set and may be customized based on the target conditions/diseases for detection and/or a particular patient. For example, the machine learning model may be trained based on input from: image data from previous 3D scans of the oral cavity (e.g., surface, color and NIR data) of the same patient or of one or more other patients; X-ray images of the oral cavity of the same patient and/or of one or more other patients, periodontal charts (e.g., including probe depths) taken of the patient and/or of one or more other patients; and/or visual inspection/tactile data from a dental professional of the patient and/or of one or more other patients. Initially, the machine learning model may be trained based on at least a minimum number of different inputs sources, which may be stored in a database of scans and patient diagnosis information. For example, in some variations, the machine learning model may be trained based on at least 3D surface data, color data and NIR image data. In other variations, the machine learning model may be trained based on at least 3D surface data, color data, NIR image data, color spectroscopy data, and NIR spectroscopy data. In other variations, the machine learning model may be trained based on at least 3D surface data, color data, NIR image data, color spectroscopy data, NIR spectroscopy data, X-ray image data, periodontal chart data, and visual inspection/tactile data. In other variations, the machine learning model may be trained based on at least 3D surface data, color data, NIR image data, color spectroscopy data, NIR spectroscopy data, and fluorescence imaging data. Once trained, the machine learning model can be used for diagnosing patients. In some examples, the machine learning model can continually be updated based on input and analyses of additional scan data.

The segmentation engine 260 can use the trained machine learning model to segment the data into individual components. In some examples the data is segmented into different tissue types (e.g., tooth, periodontium, bone, plaque, etc.), features related to different diseases or conditions (e.g., gingival inflammation, cancer lesion, precancer lesion, etc.), and/or different tooth diseases or conditions (e.g., cavities, caries, cracks, etc.). The processing system 258 may store historical or new image data in, for example, the patent database 270. The diagnosis engine(s) 268 can generate one or more diagnoses based on learned features associated with different diseases and conditions (e.g., gingival inflammation, cancer, precancer). Optionally, the treatment recommendation engine 268 can generate one or more treatment recommendations based on the one or more diagnoses. The processing system 258 can send the diagnosis and/or treatment recommendations to the display 256 (and/or other output device) for presentation to a user. In some variations, the displayed images (and/or 3D model) includes color-coded features based on the identified features indicative of a disease or condition. For example, gums effected by gingivitis, cancerous lesions, precancerous lesions, tooth cavities, tooth cracks and/or plaque may each be identified with distinctive colors.

The processing system 258 can be used to automatically detect features associated with any of a number of conditions including, but not exclusively, gum recession, tooth caries and cracks, gingivitis (e.g., based on gum color and/or inflammation), bruxism (tooth grinding), oral cancer or precancer (e.g., as evidenced by cancerous or precancerous lesions) malocclusion and bad contacts, tooth wear (e.g., based on shape of teeth, compared with normal healthy teeth), gastroesophageal reflux disease (GERD) (e.g., as evidenced by erosion of enamel, unwanted tooth movement, chipped tooth/teeth, and/or soda erosion of enamel.

The processing system 258 can be configured to automatically generate one or more diagnoses based on machine learning analysis of the scans. The system 258 may be configured to automatically chart, maintain notes, and highlight potential problems related to a diagnosis. The processing system 258 may be configured to generate 3D time lapse videos to help identify and illustrate areas in the patient's anatomy which change over time, suggest a diagnosis (e.g. chipped tooth, gingival recession, caries, etc.) based on machine learning, and generate a treatment plan (e.g., follow up appointment/scan in 6 months, night guard, etc.). The processing system 258 may be configured to analyze a 3D model and/or 2D images (e.g., 2D color and 2D NIR) to provide a diagnosis using machine learning. The processing system 258 may be configured to: identify clinical issues based on single tooth 2D color and NIR images (e.g. caries); provide a full-mouth machine learning diagnosis (e.g., identify clinical issues based on full jaw 2D and 3D data (e.g. malocclusion, tooth wear, acid reflux, etc.)); provide auto gum recession identification based on single 3D scan and 2D images; automatic chart all teeth, crowns, fillings, missing teeth etc. based on 3D scan; and/or automatically identify prepped teeth and type of restoration (crown, inlay, bridge, etc.) based on 3D scan.

The dataset(s) for building the machine learning may be collected and iteratively modified over time based on a particular patient's oral scans and/or a library of oral scans of different patient. In some variations, the system 258 may be configured to build a questionnaire to identify clinical issues and recommend treatment, identify doctors that would qualify and annotate the dataset, and train machine learning models using the datasets.

Figure 12A:
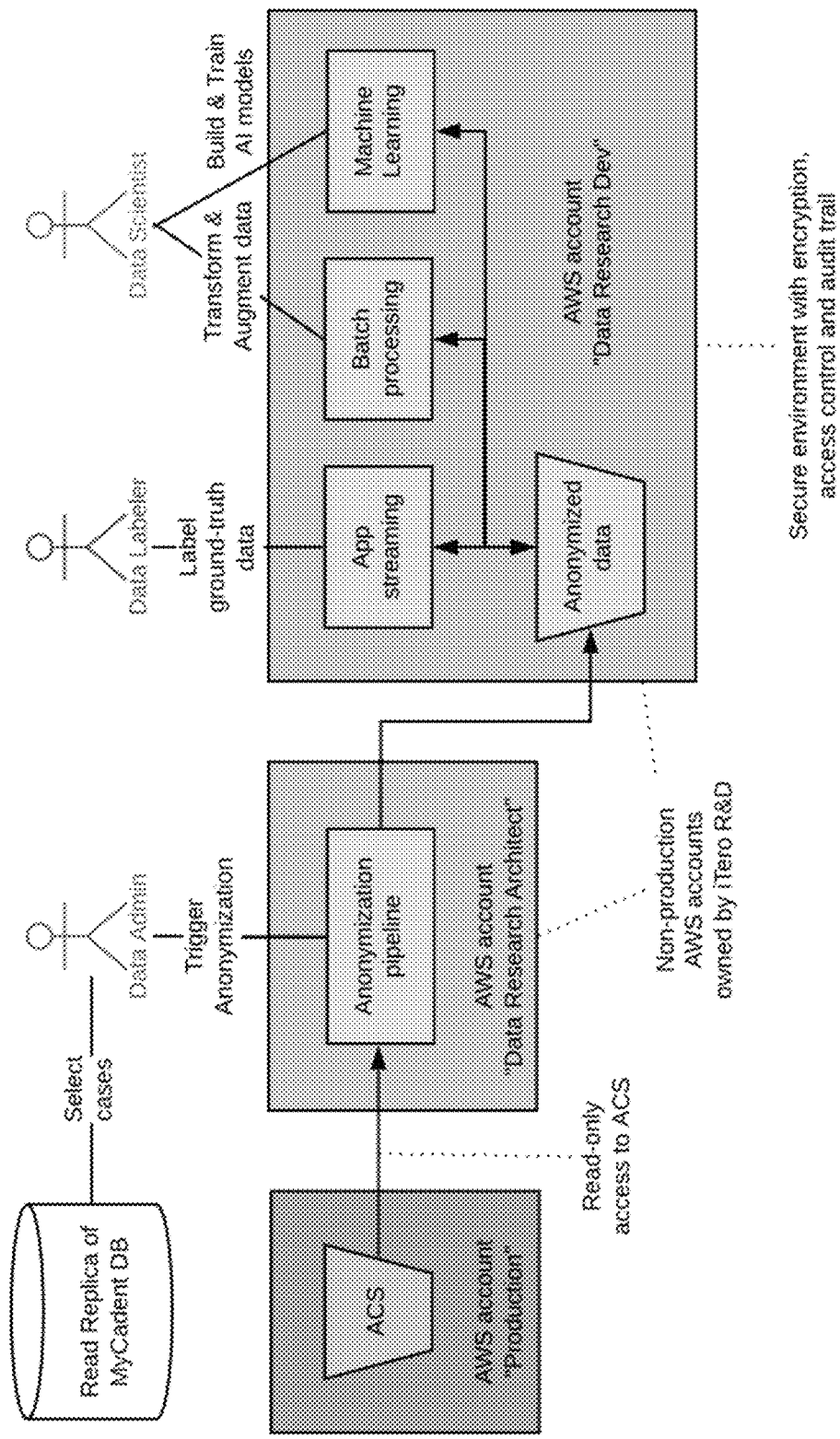
FIG. 12A-12C illustrate a machine learning architecture.
Figure 12B:
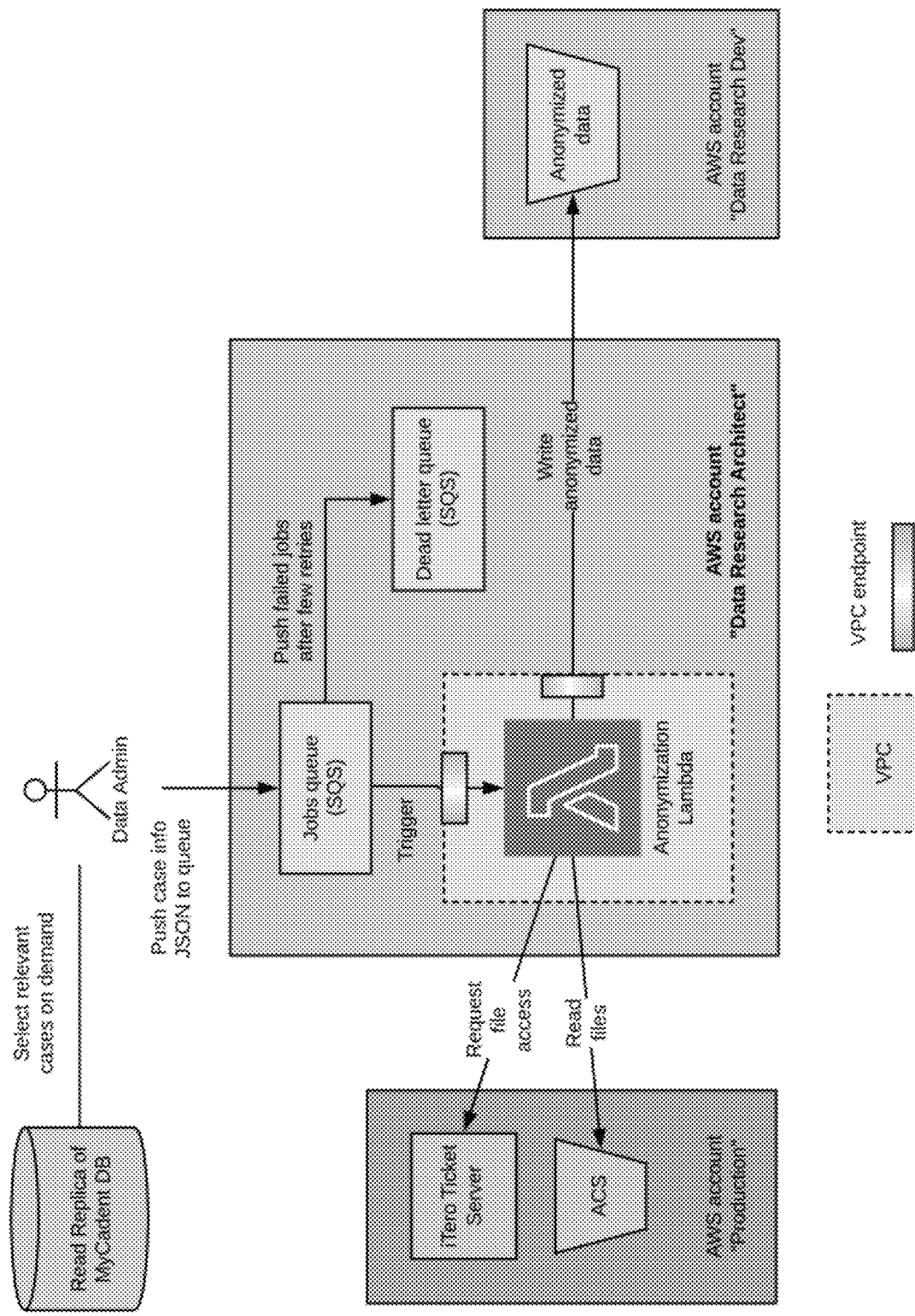
Figure 12C:
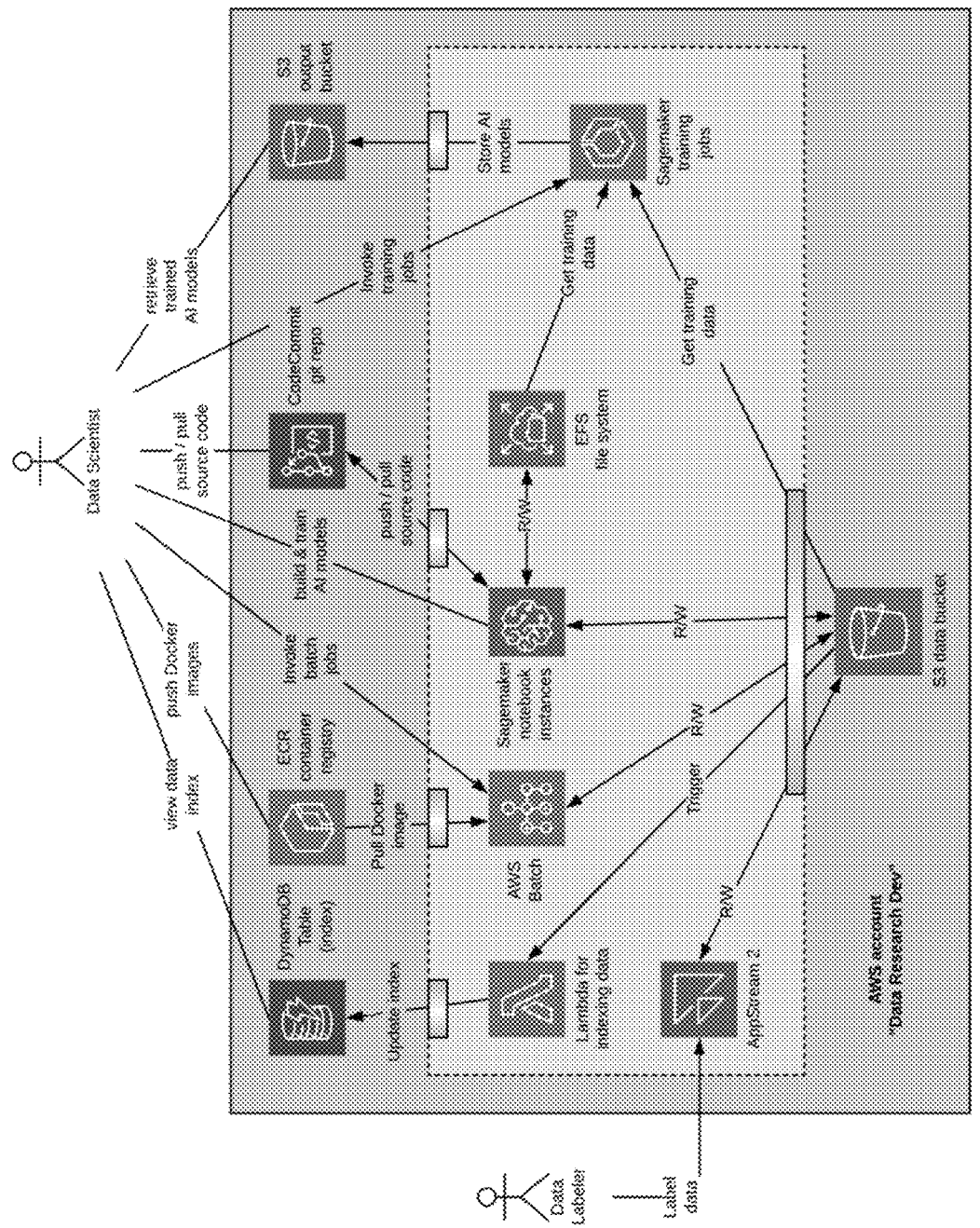
Figure 13A:
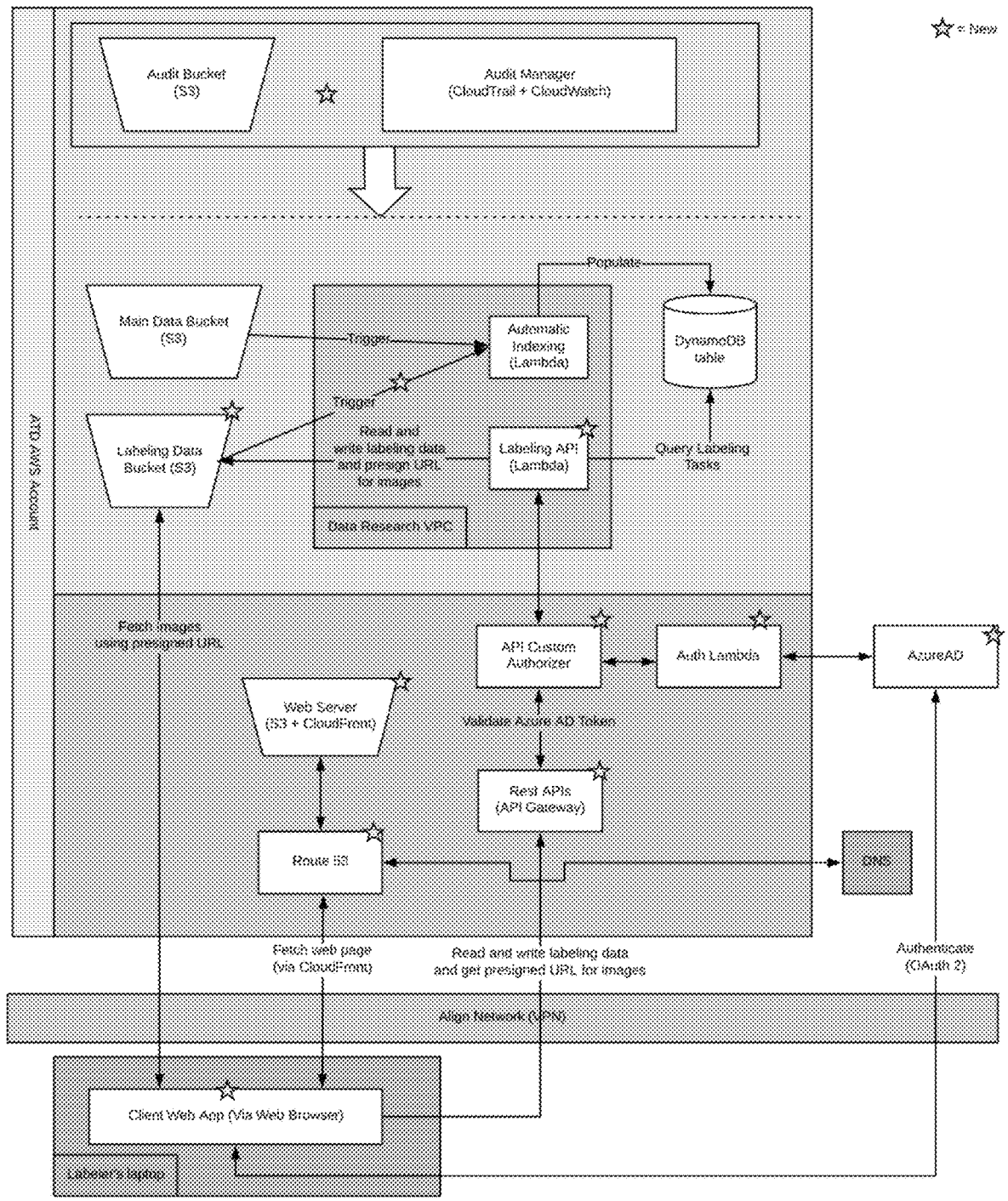
FIGS. 13A-13F illustrate architecture diagrams for a labeling engine.
Figure 13B:
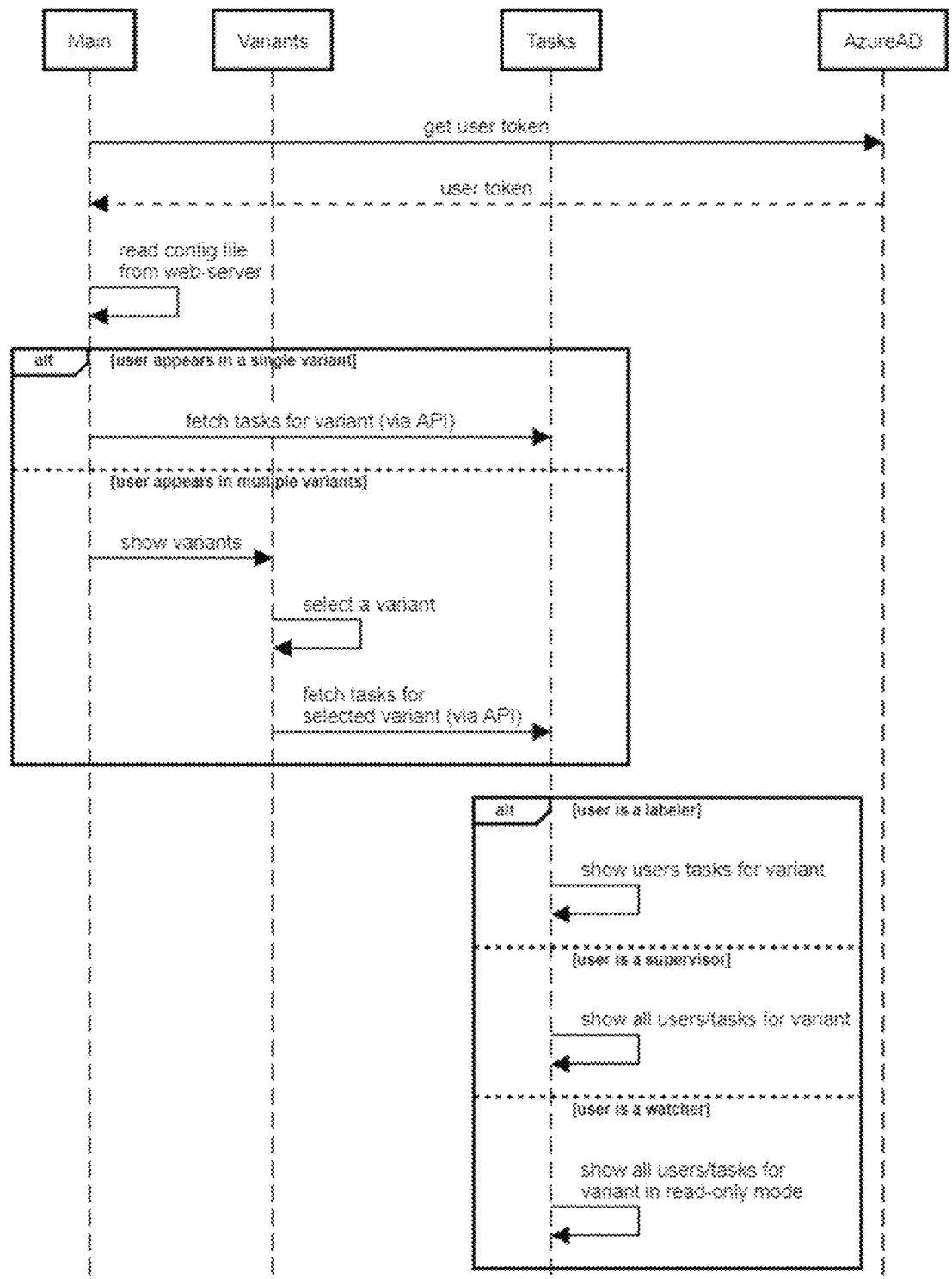
Figure 13C:
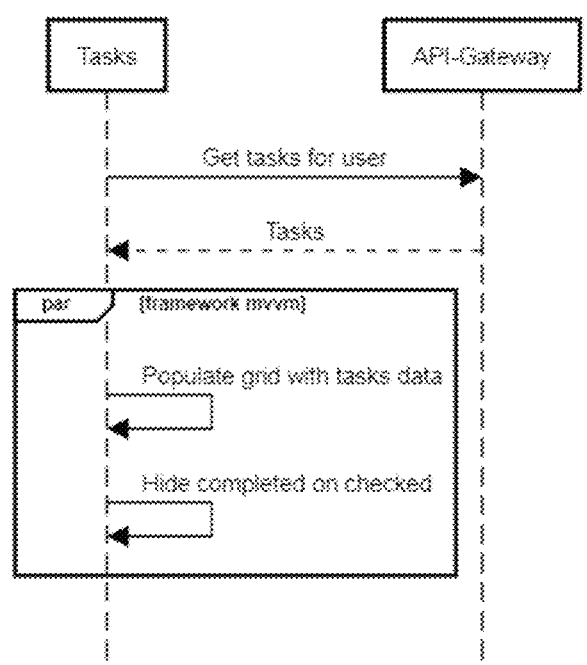
Figure 13D:
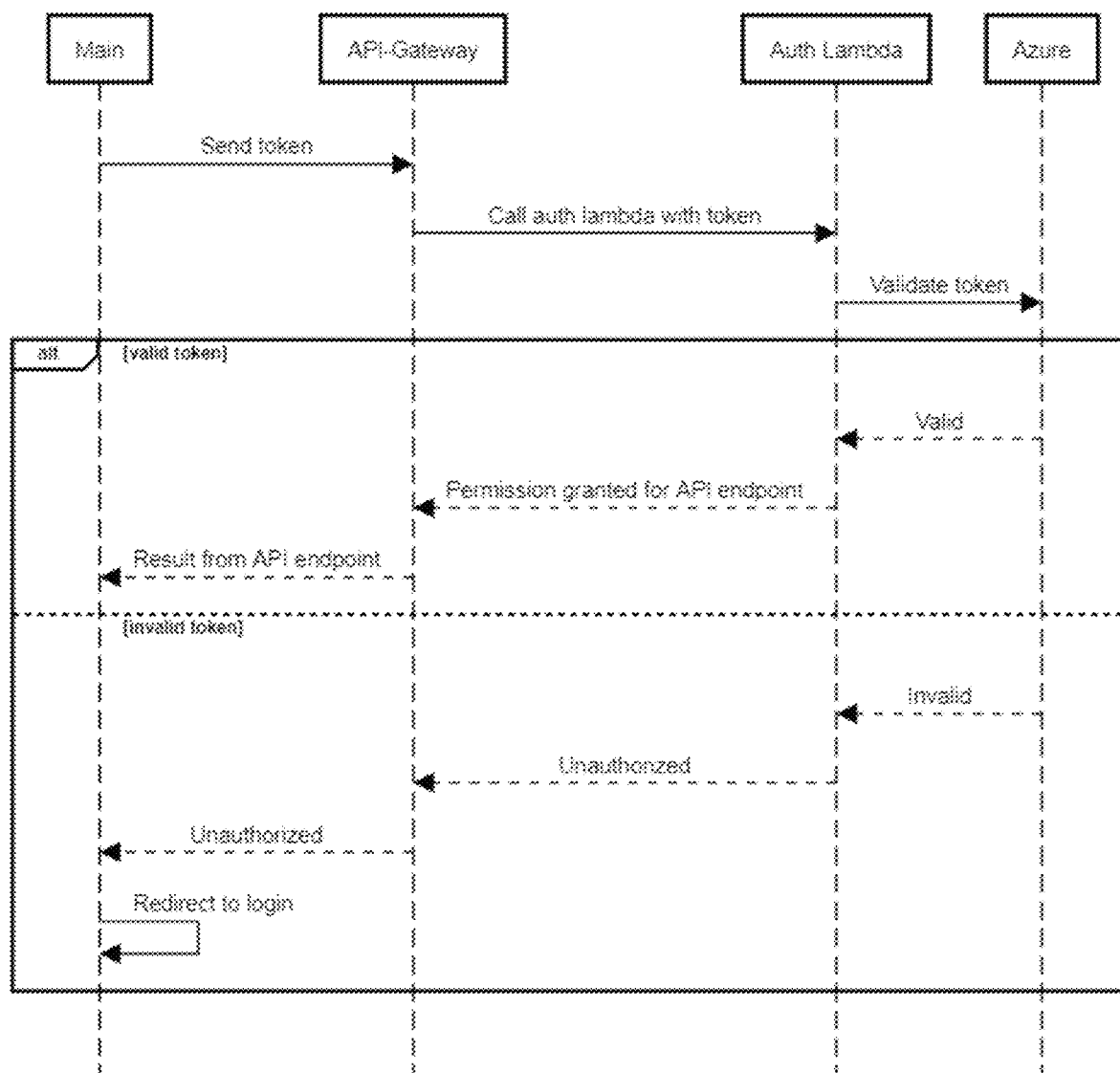
Figure 13E:
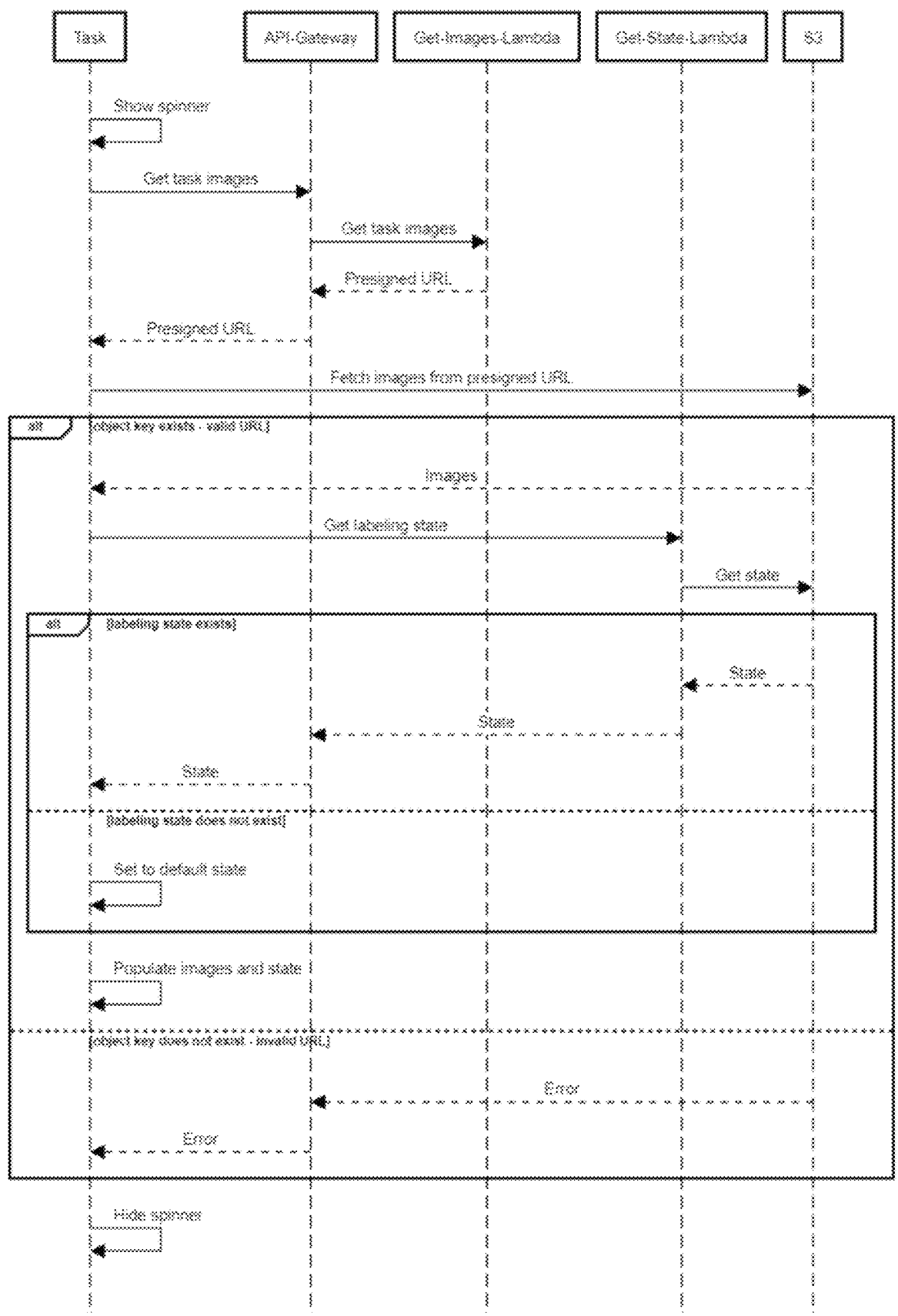
Figure 13F:
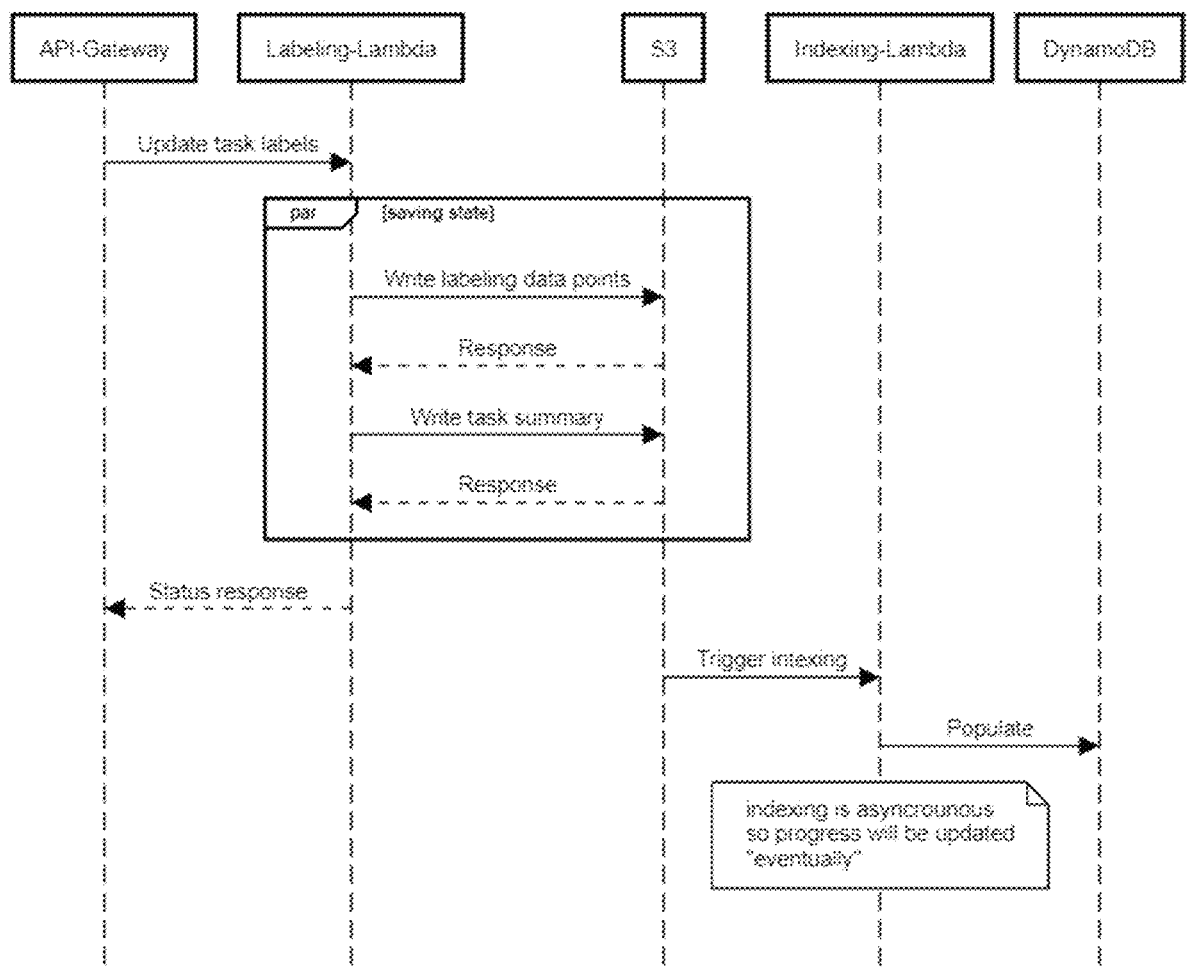

FIG. 12A-12C illustrate high-level diagrams of an example machine learning architecture. FIGS. 13A-13F illustrate architecture and data flow diagrams for an example labeling engine.

Figure 14A:
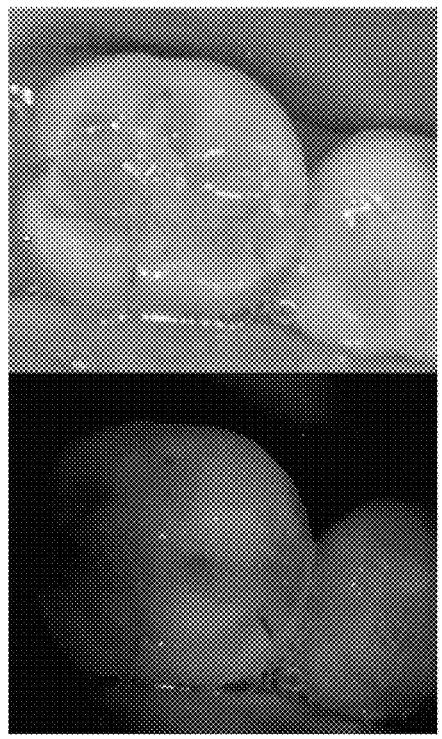
FIGS. 14A and 14B illustrate examples of NIR images and color images illustrating how features associated with dental caries can be labeled using a labeling engine.
Figure 14B:
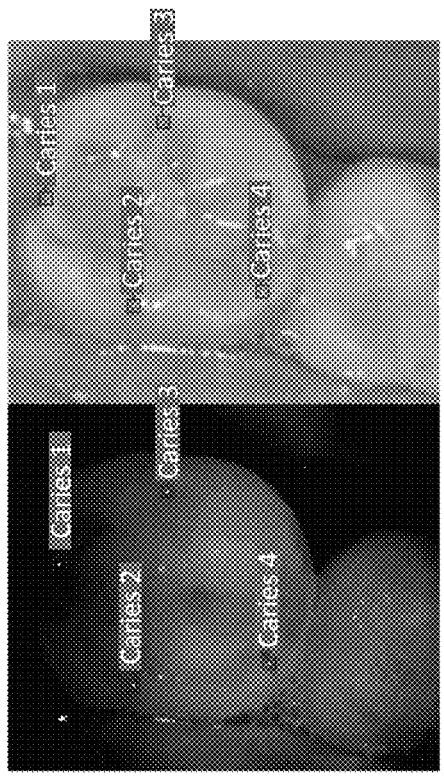

FIGS. 14A and 14B show examples internal structure (NIR) images and color images illustrating how features associated with dental caries can be labeled using the labeling engine. The labeling engine may be used to train the machine learning model by assigning labels to features identified in the images as being associated with a disease or condition. For example, features associated with dental caries can be identified and labeled in the internal structure (NIR) image. The labeling engine can be configured to compare a color image taken at the same position (same field of view) as the internal structure (NIR) image to locate the same dental caries in the color image. FIG. 14A shows the internal structure (NIR) images and color images before labeling and FIG. 14B shows the images after the dental caries are marked and labeled (Caries 1, Caries 2, Caries 3, and Caries 4). The labeling engine may then be used to compare internal structure (NIR) images and color images taken at different corresponding positions (field of views) to correlate and label dental caries in all the teeth. This process can be repeated with other scanned images to teach the machine learning model how to identify dental caries in NIR and color images. One or more additional labeling engines may be used to compare NIR and color images, and in some cases other imaging modalities (e.g., 3D surface imaging and/or fluorescence imaging), to identify and label features associated with other oral conditions (e.g., gum inflammation, pre-cancer, cancer, etc.), which can be used to teach the machine learning model how to identify the other oral conditions. In some cases, the color and/or NIR data is processed to extract spectral data to identify and label the features associated with the oral conditions, which may also be used to teach the machine learning model.

Machine Learning Training—Image Selection

Figure 17A:
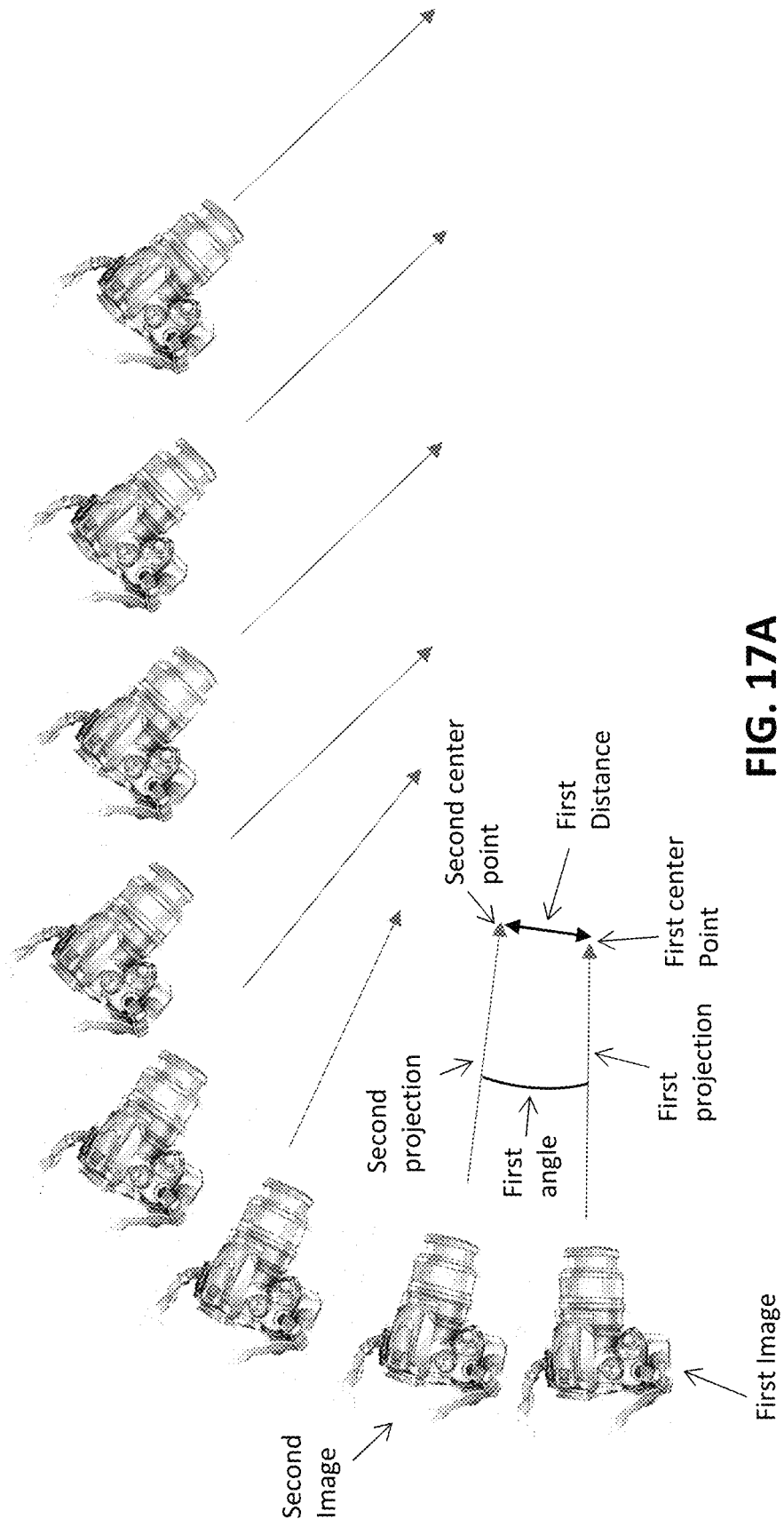
FIGS. 17A-17E schematically illustrate how a subset of images from a scan may be selected.

In some cases, the machine learning model is trained using a subset of collected images of a scan. Using a subset of the images can improve the efficiency of training the machine learning model. FIGS. 17A-17D schematically illustrate how a subset of images from a scan may be selected. FIG. 17A shows various positions of a scanner sensor (e.g., camera) as it progressively scanned around an object (e.g., dental arch). For every image captured by the scanner sensor, there is center point along the projection of the center pixel with a fixed distance. The fixed distance typically ends around the target being imaged, but not necessarily. At an initial stage (stage 0), all the images captured by the scanner are available. When training the machine learning model, a first image that is captured by the scanner sensor at a first position of the scanner sensor is selected. If a second image captured by the scanner sensor at a second position is determined to be too close to the first image at the first position, then the image collected at the second position is not used in training machine learning model. In some cases, a first position of the scanner sensor is too close to the second position if a first angle between a first projection from the center pixel of the first image and a second projection from the center pixel of the second image is smaller than a threshold angle and if and a first distance between the first center point distance of the first pixel and the second center point distance of the second pixel is less than a threshold distance. In this case, the first angle is determined to be less than the threshold angle and the first distance is determined to be less than the threshold distance. Therefore, the second image is determined to be too close to the first image and is not used in training of the machine learning model.

Figure 17B:
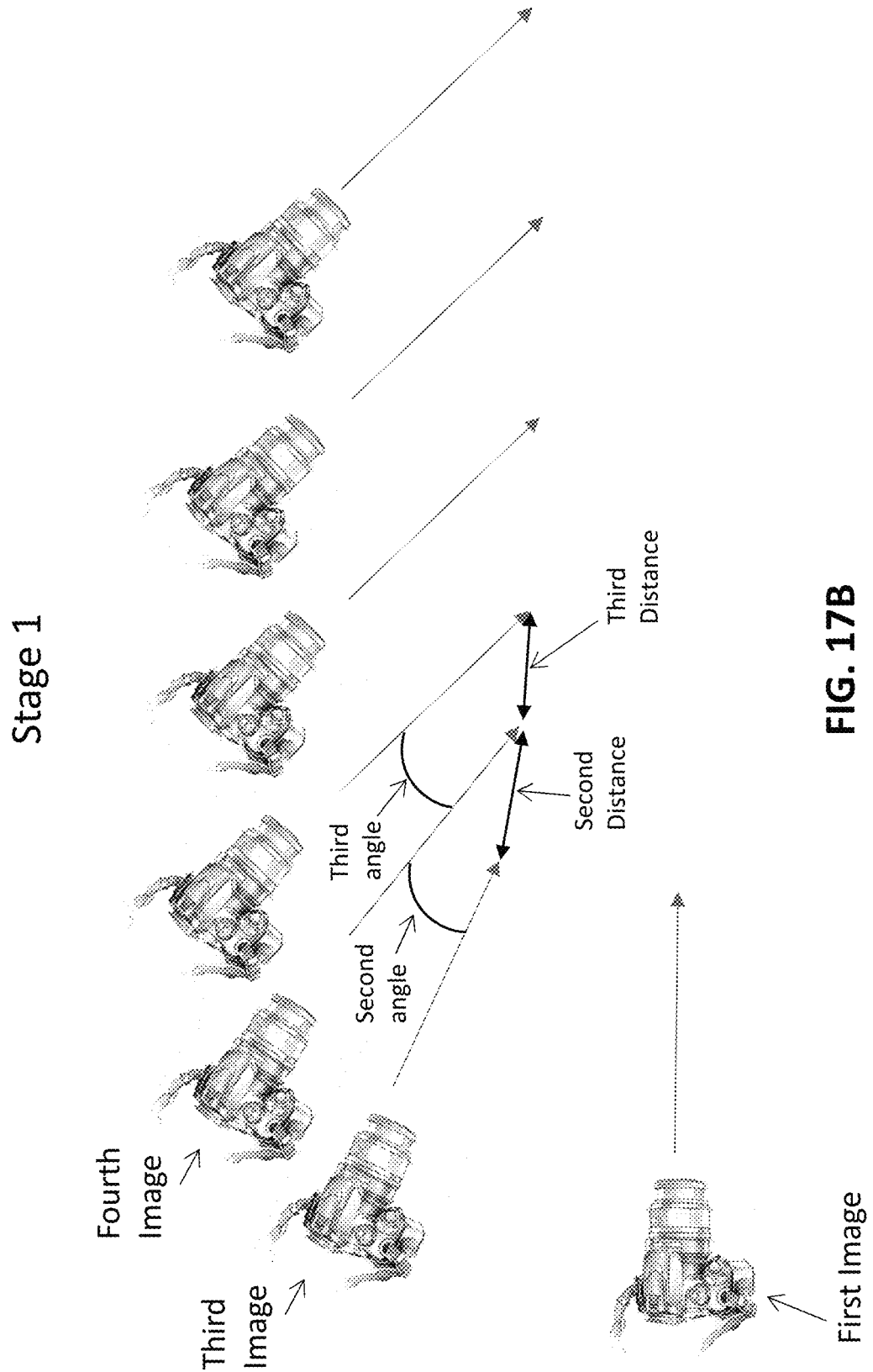
Figure 17C:
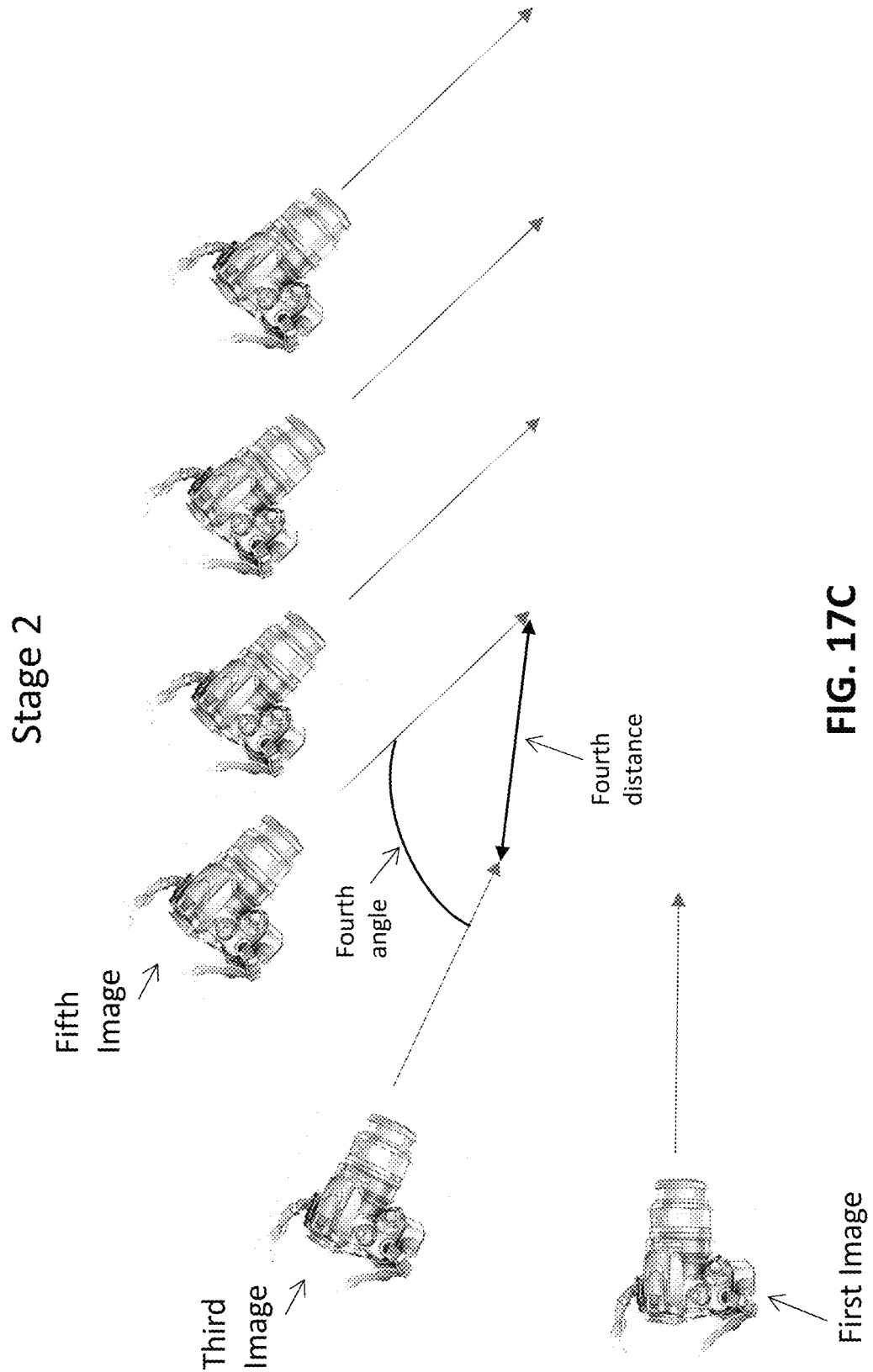
Figure 17D:
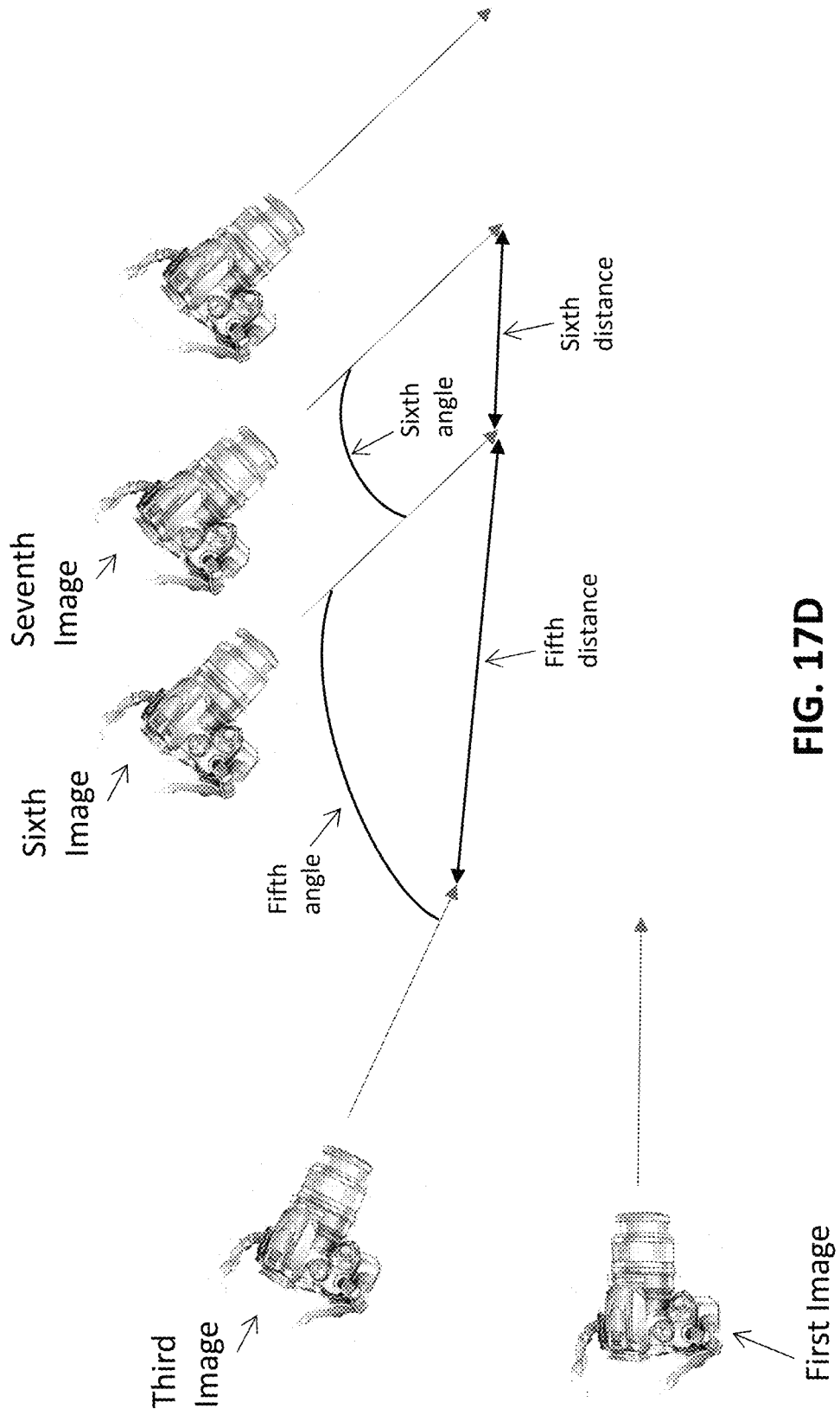
Figure 17E:
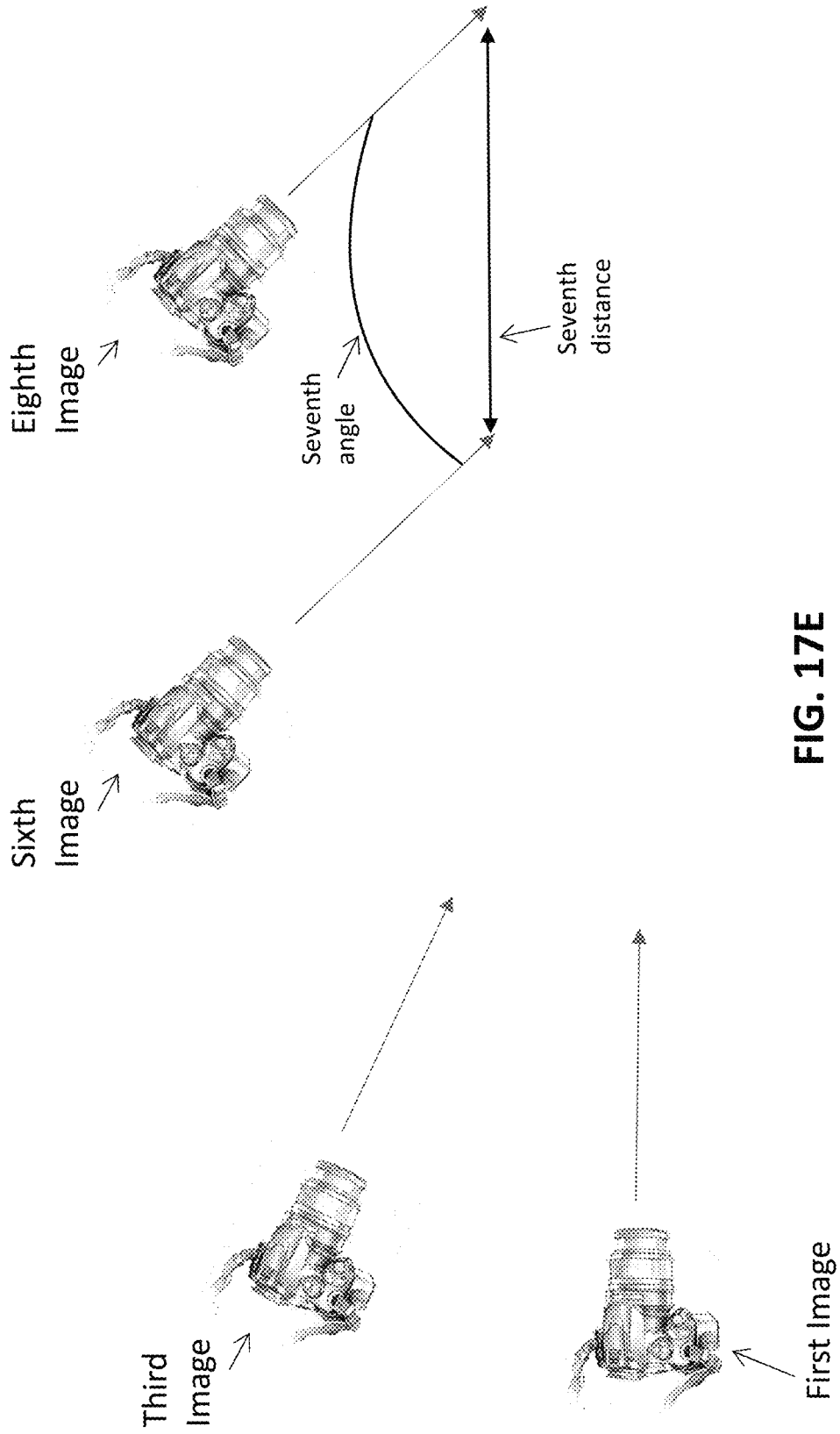

FIG. 17B shows the second image removed. Each image is similarly analyzed to determine which images are too close and not used in training the machine learning model. For example, a third image captured by the scanner at a third position is determined to be acceptably far apart from first position of the scanner where the first image was captured since a second angle is equal to or greater than the threshold angle and the second distance is greater than the threshold distance. Therefore, the third image is used in training the machine learning model. A fourth image captured by the scanner sensor at fourth position of the scanner sensor is determined to be too close to the third position of the scanner sensor since a third angle is less than the threshold angle and a third distance is less than the threshold distance. Thus, the fourth image is not used in training of the machine learning model, as shown in FIG. 17C. A fifth image captured by the scanner at fifth position of the scanner sensor is determined to be too close to the third position of the scanner since a fourth angle is less than the threshold angle and a fourth distance is less than the threshold distance. Thus, the fifth image is not used in training of the machine learning model, as shown in FIG. 17D. A sixth image captured by the scanner at a sixth position is determined to be acceptably far apart from third position of the scanner sensor where the third image was captured since a fifth angle is equal to or greater than the threshold angle and a fifth distance is greater than the threshold distance. Therefore, the sixth image is used in training the machine learning model. A seventh image captured by the scanner sensor at seventh position of the scanner sensor is determined to be too close to the sixth position of the scanner since a sixth angle is less than the threshold angle and a sixth distance is less than the threshold distance. Thus, the seventh image is not used in training of the machine learning model, as shown in FIG. 17E. An eighth image captured by the scanner at an eighth position is determined to be acceptably far apart from sixth position of the scanner sensor where the sixth image was captured since a seventh angle is equal to or greater than the threshold angle and a seventh distance is greater than the threshold distance. Therefore, the eight image is used in training the machine learning model.

The example of FIGS. 17A-17E shows how the subset of four images can be selected from eight images based on distance and angle of image capture positions of the scanner and used as a training data set to train a machine learning model. In practice, the machine learning model may use a different threshold angle and distance based on design requirements. In some applications, the threshold angle between the images may range from about 1° to about 10° (e.g., 1°-10°, 1°-5°, 5°-10°, 4°-6°, 3°-7°, or 2°-8° and the threshold distance between the images may range from about 1 mm to about 10 mm (e.g., 1 mm-10 mm, 1 mm-5 mm, 5 mm-10 mm, 1 mm-3 mm, 2 mm-4 mm, or 1 mm-4 mm).

The threshold angle and distance techniques described above can also be used to filter images when using the trained machine learning model to analyze images. For example, the images from a scan take from a patient's oral cavity may be filtered using these techniques before using the trained machine learning model to analyze the filtered images and detect features indicative of a disease or condition (e.g., gingival inflammation, cancer lesion, precancer lesion, etc.). This may be useful in situations where there are too many scan images and/or to improve performance issues of running the trained machine learning model.

Gingival Inflammation Detection and Severity Determination

Figure 3:
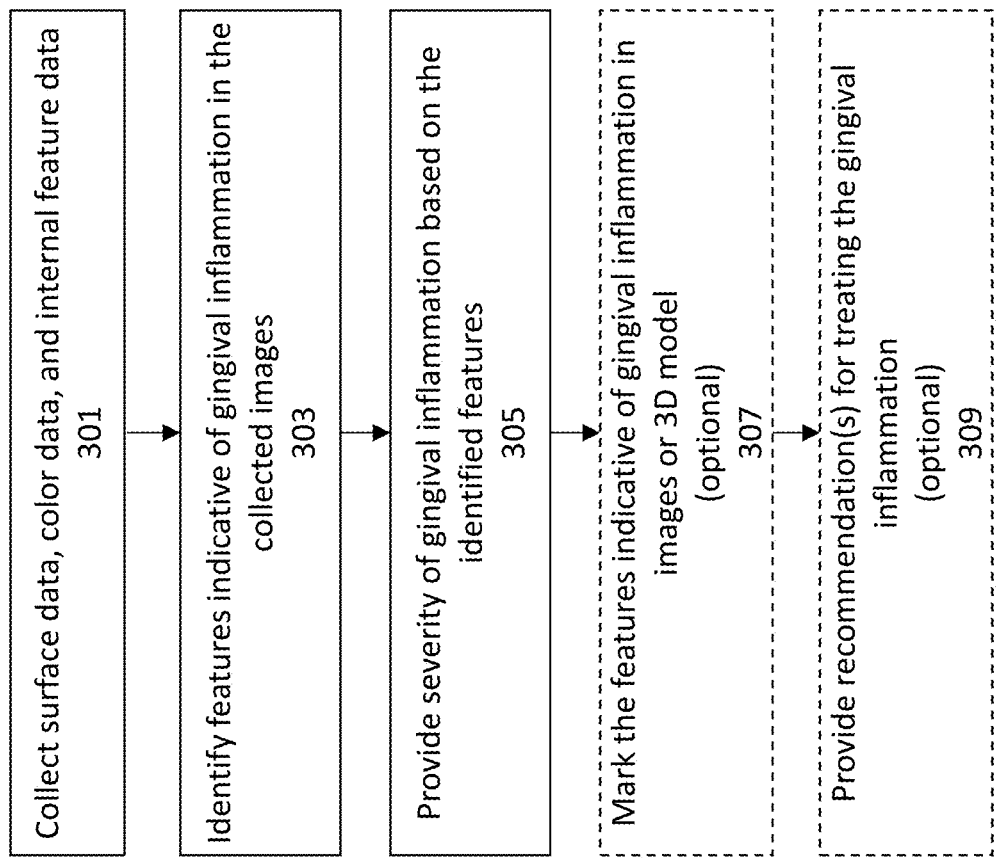
FIG. 3 is a flowchart indicating an example method for identifying features indicative of gingival inflammation based on oral scans.

The intraoral scanning systems described herein can be used to non-invasively detect gingival inflammation and determine a severity of gingival inflammation based on the various image data collected using different scanning modalities. In some cases, this information can be used to provide a diagnosis of a periodontal disease. FIG. 3 is a flowchart illustrating an example method for identifying features indicative of gingival inflammation and providing a severity of the inflammation based on oral scans. The intraoral scanner can be used to scan the patient's mouth to collect surface data, color data, internal feature data 301. As described previously, the surface data can include image data associated with illuminating the target (e.g., periodontium and/or teeth) using a first wavelength range of light, which can include non-visible wavelengths and/or visible wavelengths (e.g., at or around 680 nm, or other appropriate wavelengths). The color data can include image data associated with illuminating the target using a second wavelength range of light (e.g., white light). The internal feature data can include image data associated with illuminating the target using a third wavelength range of light, which include penetrative wavelengths of light (e.g., IR, e.g., NIR).

In general, captured data may be stored and saved in the same coordinate system. For example, surface data (including 3D surface model data) may use a coordinate system (e.g., x, y, z) (e.g., so that the 3D surface model is $S(x,y,z)$) and the internal feature (penetrative) data may use or reference the same coordinate system (e.g., so that the internal feature data is $I(x, y, z)$). Thus, common features or structures may have the same address (coordinates) between both data sets. Likewise, the color data may use the same coordinate system as the surface data and internal feature data. In practice, recording the data collected using different modalities in the same coordinate system may be achieved by scanning at the same position and/or time. As mentioned, in a hand-held user controlled intraoral scanning device (e.g., wand) it may be difficult to scan the same region at different times in different wavelengths. Thus, any of the apparatuses and methods described herein may coordinate scanning at the different modalities or modes (e.g., surface data scanning and/or internal features/penetrative data scanning).

Once collected, the data may be analyzed, and/or filtered (including subtracting, smoothing, etc.), or otherwise processed. In some cases, the data is combined to form a 3D model rendering of the intraoral cavity (e.g., gums, teeth, jaw, etc.), or a portion of the intraoral cavity, using data from the different scanning modalities (e.g., surface, color and/or NIR). For example, when building a 3D geometry based on the internal feature data (which is typically 2D in nature), the algorithm may use the reference to the known 3D surface scan to improve the accuracy of the internal feature data, and/or color data. In general, in any of the apparatuses and methods described herein, the internal feature data collected may be used to reconstruct a volumetric model of the tooth or teeth including the internal features. For instance, tomographic reconstruction (e.g., optical tomography) may be used. In some variation, the methods and/or apparatus may divide the volume of the tooth into small voxels and for each voxel, estimate these four parameters (refraction index, reflection, scattering, absorption) based on the imaging data collected, using the coordinate system corresponding to the coordinate system of the surface data. Alternatively or additionally, multi-surface modeling may be used, which assumes optical properties of a set of materials, such as air, gingiva, periodontal ligament fiber, bone, dentin, and enamel, to find boundaries between the materials. Alternatively or additionally, a contour line method may be used in which a first boundary (e.g., air-gingiva boundary) is given from the 3D surface capture, and then, by finding the edges of regions in the 2D penetrating images, a smooth 3D surface may be approximated that best fits this silhouette. Examples of systems and methods of forming a 3D model based on oral scans are described, for instance, in U.S. Pat. No. 10,123,706, which is incorporated herein by reference in its entirety. The images can be segmented to distinguish among different anatomical surfaces structures of the patient's mouth, including those features indicative gingival inflammation.

Once the oral scan data is received or otherwise accessed, one or more features in the scan data indicative of gingival inflammation are identified 303. This can involve comparing the scan image data to previously collected data and using machine learning model (e.g., trained network) to identify and distinguish anatomical features (e.g., teeth, gums, connective tissue, bone etc.) as well as features of indicative of gingival inflammation. Such comparison may be automatic, semi-automatic or manual. As described above, the previously collected data used to train the machine learning model may include image data from previous 3D scans (e.g., including surface, color, NIR image data, and/or NIR spectroscopy data), X-ray images, periodontal charts (e.g., including probe depths), and/or visual inspection/tactile data from a dental professional.

In one example, the cementoenamel junction (CEJ) of one or more teeth in the scan data (e.g., in the 3D model) are identified and measured to determine an extent of gum recession. For example, a distance between the gums and a tooth in the segmented data can be measured to determine whether the distance is indicative of significant gum recession associated with gingival inflammation. In another example, the 2D color data are analyzed to determine whether the color of the gums is sufficiently red to indicate early stages of gingival inflammation. The scan data may also be analyzed to determine the size and shape of the gums to determine whether the gums is sufficiently swollen/inflamed as an indication of gingival inflammation. In a further example, the dental pocket (groove between gums and teeth) at several locations can be identified and measured (e.g., in the 3D model) to determine the pocket depth (similar to dental probe measurements done in dental offices). Deep pocket depths can indicate gum recession and/or bone loss due to gingival inflammation. In another example, NIR spectroscopy is used to determine blood serum concentration as indicative to inflammation, which may be associated with gingival inflammation.

The intraoral scanning system can provide a severity of gingival inflammation based on the identified features 305. The severity may be based on a combination of features identified as being associated with gingival inflammation and the extent of the identified features. For example, if the scan data indicate swollen and red gums but only minor gum recession as determined by CEJ and pocket depth measurements, the system may determine that the patient may have mild to moderate gingival inflammation. On the other hand, if the scan data indicate severely swollen and red gums and severe gum recession as determined by CEJ and pocket depth measurements, the system may determine that the patient may have severe gingival inflammation. The severity of gingival inflammation can be determined based on standard dental classifications of gingivitis (e.g., gingivitis I, II, III, IV and V)g. This information can be evaluated by a specialist for verification as to a proper diagnosis, for example of a periodontal disease.

In some variations, the features indicative of gingival inflammation may be marked on images or on a 3D model 307. For example, the features may be highlighted (e.g., using one or more colors) and/or labeled (e.g., using with symbols and/or lettering) on images or the 3D model as displayed on a display of the intraoral scanning system. In some variations, the system can be figured to provide one or more recommendations for treating the gingival inflammation based on the identified level of gum inflammation 309.

In some case, the recommendation may include a recommendation for one or more follow up appointments to recheck the patient's oral health.

Figure 4:
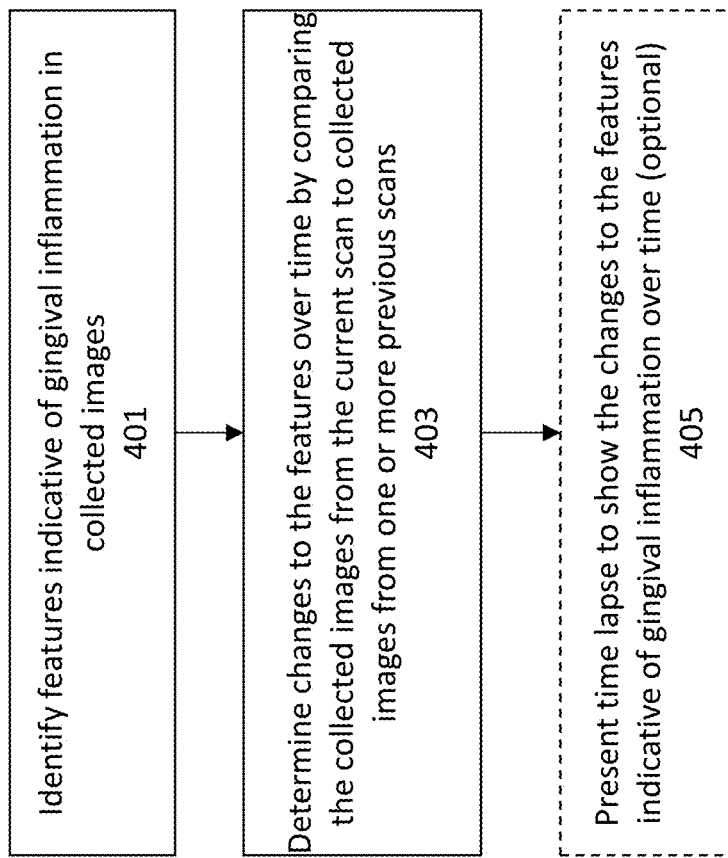
FIG. 4 is a flowchart illustrating an example method for tracking changes to a patient's oral condition over time.

FIG. 4 is a flowchart illustrating an example method for tracking changes to a patient's oral condition over time. Such method may be performed to monitor the patient's oral health to assure that mild gingival inflammation does not progress, or to monitor the patient's recovery during treatment of gingival inflammation. At 401, features indicative of gingival inflammation are identified in the collected images from a current intraoral scan of the patient. At 403, the collected images from the current scan are compared to collected images from one or more previous scans of the patient to determine changes to the features over time. For instance, collected images from a current scan of the patient's oral cavity can be compared to collected images from scans previously performed on the same patient's oral cavity (e.g., from previous dental office visits). In one example where the patient's oral health is being monitored to assure that the symptoms of gingival inflammation do not worsen, the images from the current scan may be compared with images from previous scans to determine whether CEJ and pocket depth measurements indicate improving or worsening gum recession and whether gum color/size measurements indicate improving or worsening gum inflammation/irritation. In another example where the patient is being treated for gingival inflammation and monitored to determine whether the treatment is effective, the images from the current scan may be compared with images from previous scans to assure that CEJ and pocket depth measurements indicate improving gum recession and that gum color/size measurements indicate less gum inflammation/irritation. In some cases, the extent of gingival inflammation can be updated based on the changes.

At 405, the system can optionally present a time lapse to show the changes to the features indicative of gingival inflammation in a condensed time frame. For example, time lapse presentation may be used to illustrate changes in the mucogingival line, which are associated with gum recession. The time lapse presentation may also be used to detect color, size and/or shape changes to the gums over time due to increasing or decreasing inflammation.

Example Gingival Inflammation Detection Using Visible Spectral Data

Figure 16A:
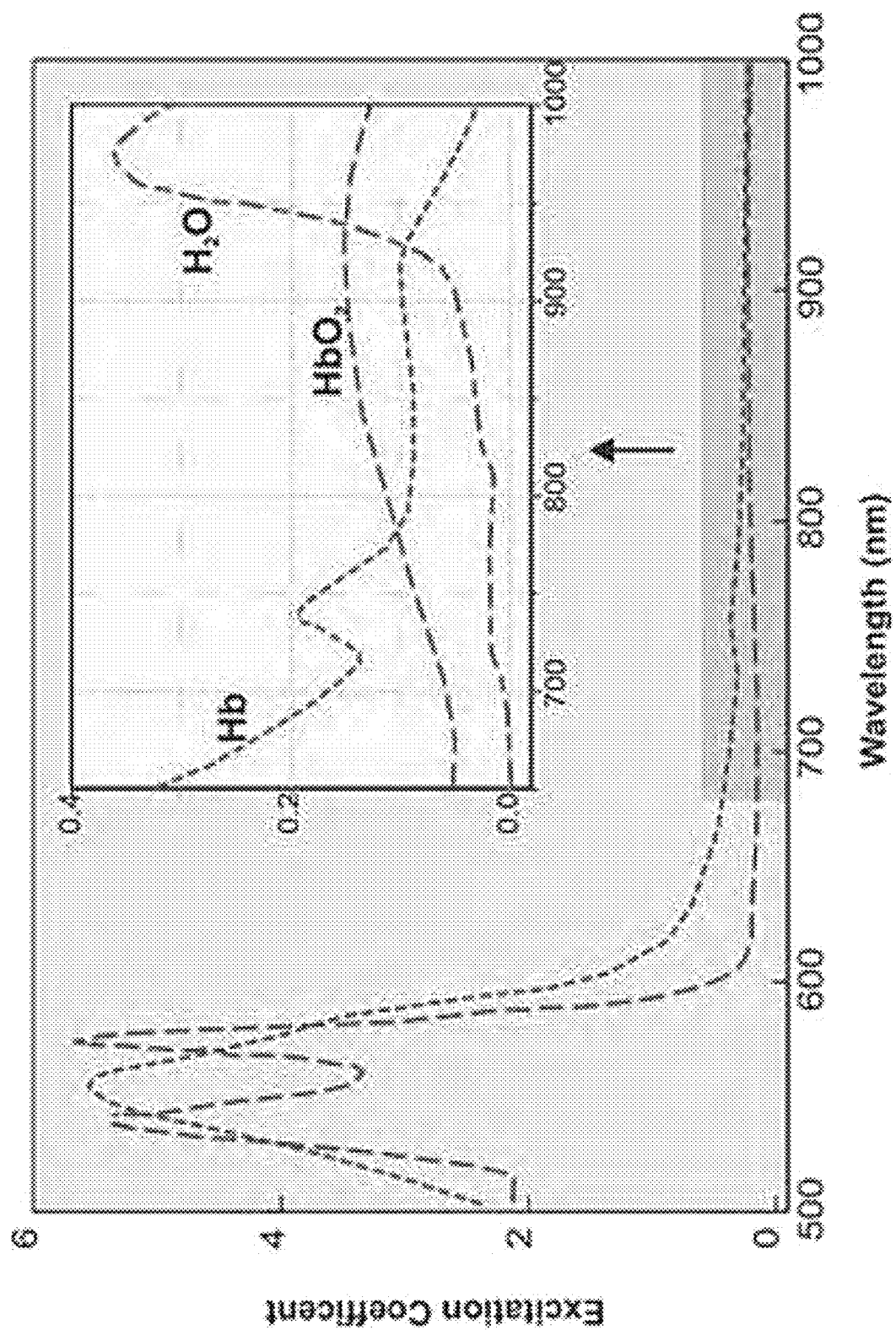
FIGS. 16A-16H illustrate an example of the extraction of spectral data from color (visible) image data and used to identify features indicative of gingivitis.
Figure 16B:
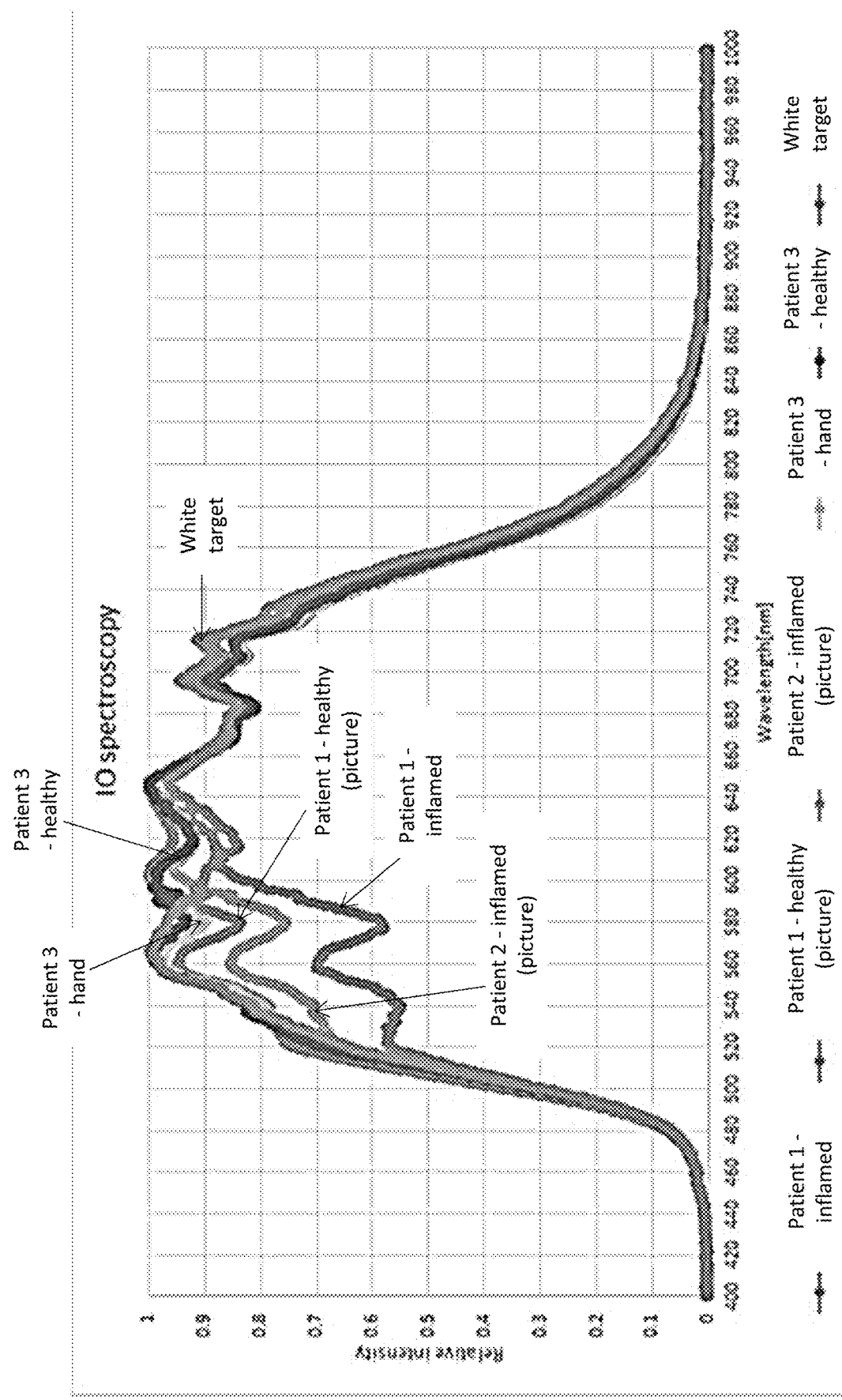
Figure 16C:
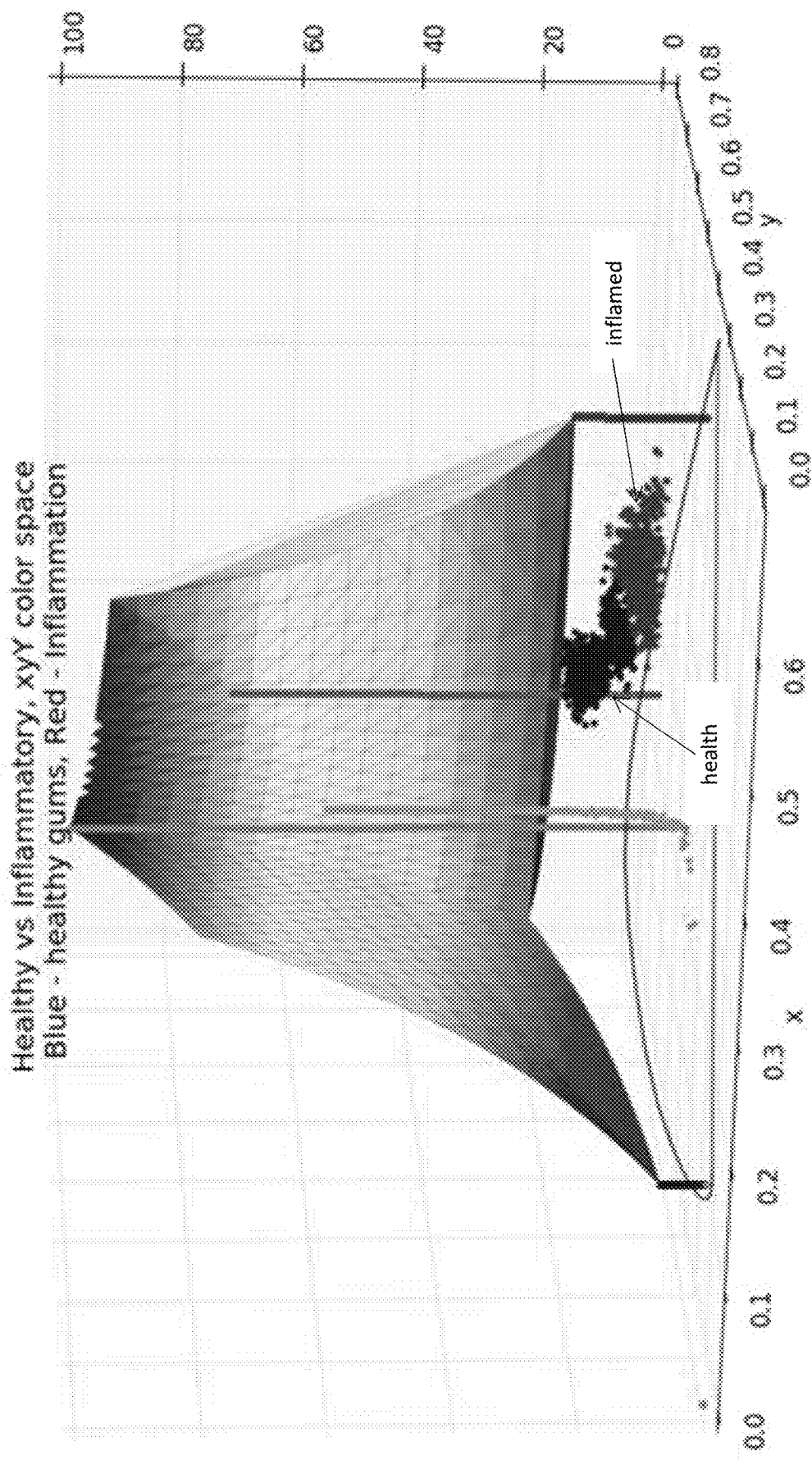
Figure 16D:
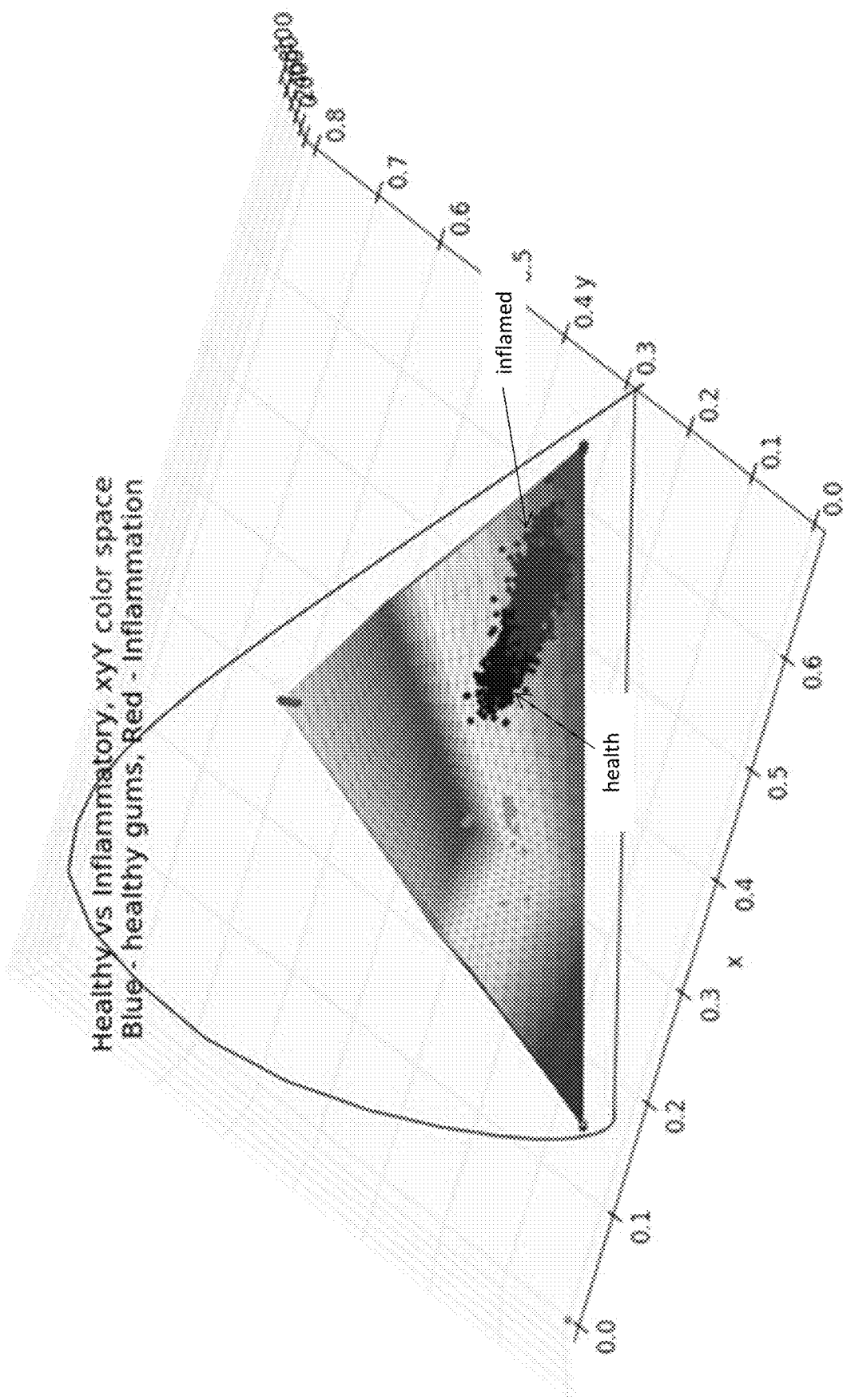
Figure 16F:
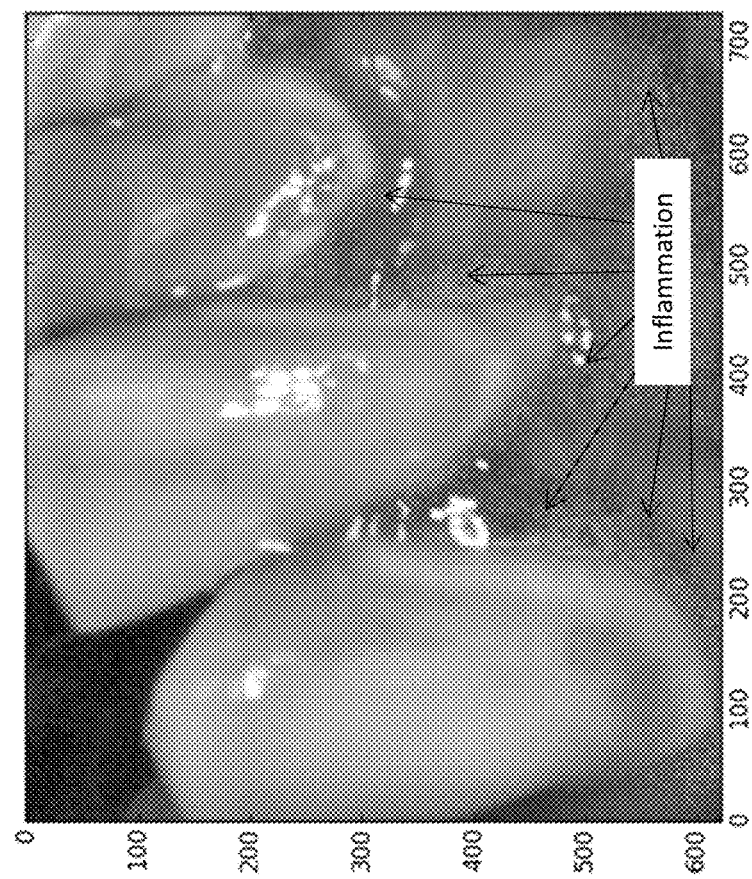
Figure 16E:
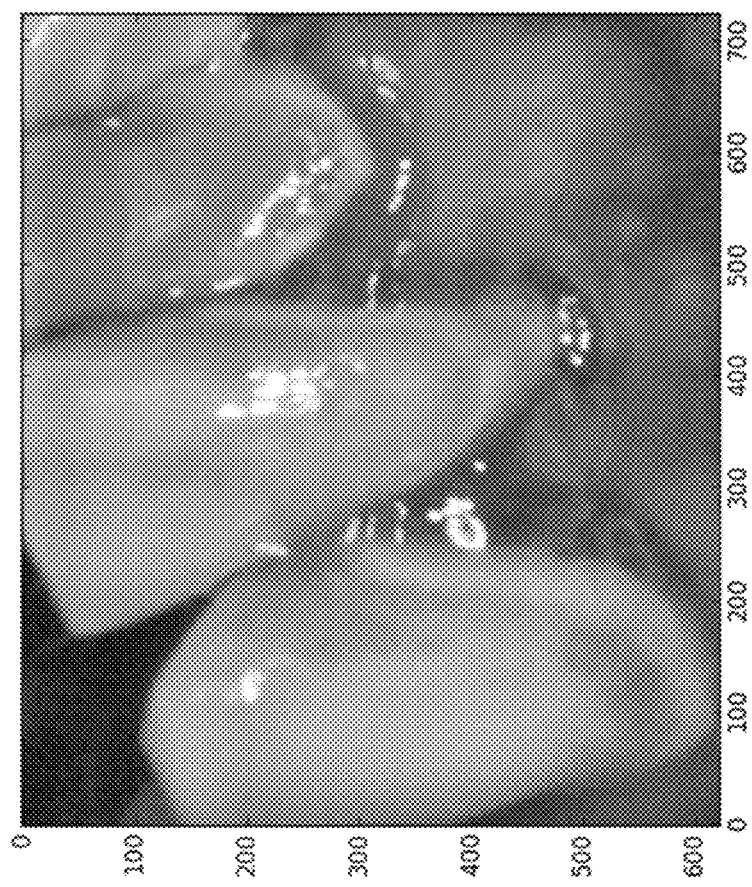
Figure 16H:
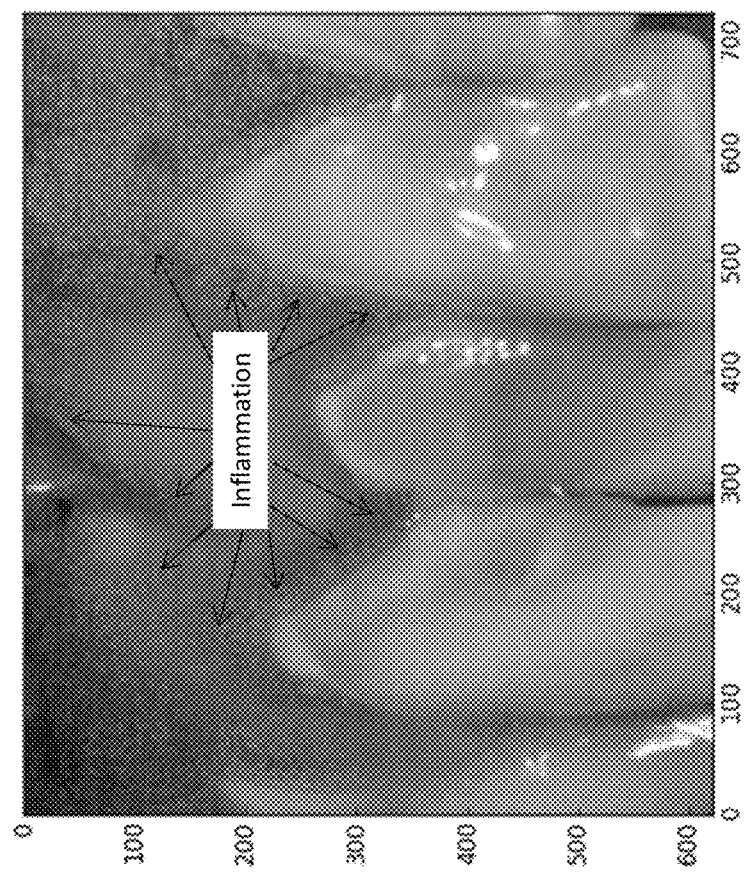
Figure 16G:
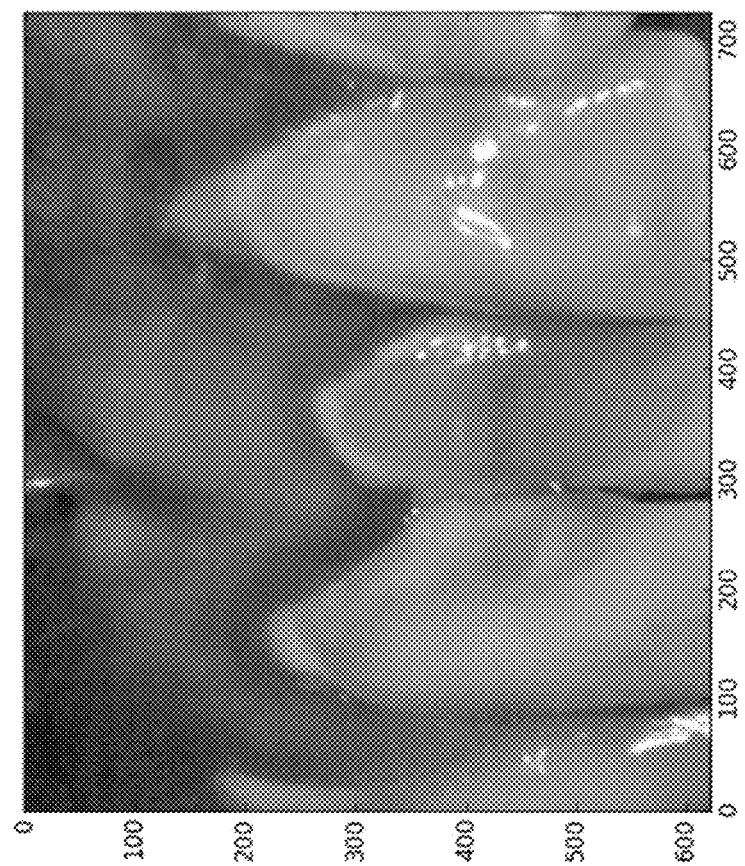

In some examples, spectral information is extracted from the image data and analyzed to identify features indicating gingival inflammation. FIGS. 16A-16H illustrate an example of how spectral data extracted from color (visible) image data and used to identify features indicative of gingivitis. FIG. 16A is a graph of excitation coefficient as a function of wavelength, indicating a noticeable spectral different between various levels of gingival inflammation in the 500-800 nm spectral band due to oxygen depletion in inflamed gingiva. FIG. 16B is a graph showing how spectral data from the color image data collected by the scanner indicates differences of oxygen content of healthy gingiva versus inflamed gingiva, thereby allowing for sensitivity assessment for gingival inflammation. FIGS. 16C and 16D show the color data of FIG. 16B graphed in a CIE xyY color space diagrams per color/saturation contents, with the inflamed group in red and distinctive from the healthy group in blue. These color differences can be used to mark features in the color images that indicate gingival inflammation. FIG. 16E shows a color image of a portion of the gingiva and FIG. 16F shows the same color image with color markings indicating locations in the gingiva with inflammation. FIG. 16G shows another color image of a portion of the gingiva and FIG. 16H shows the same color image with color markings indicating locations in the gingiva with inflammation. These types of visible spectral analyses can be used to train the machine learning model to identify color-based indications of gingival inflammation in color data collected by the scanner. In addition, the data can be used to identify different severities of gingival inflammation based on differing coloring (oxygen content). Similar analysis can be used to identify indications of gingival inflammation using spectral analysis of the NIR image data. In some cases, 3D surface, color and NIR data is combined for the analysis and training of the machine learning model. In some instances, statistical analysis is performed on the collected data, which may be used to determine a probability of gingival inflammation.

Oral Cancer and Precancer Detection and Diagnoses

Figure 5:
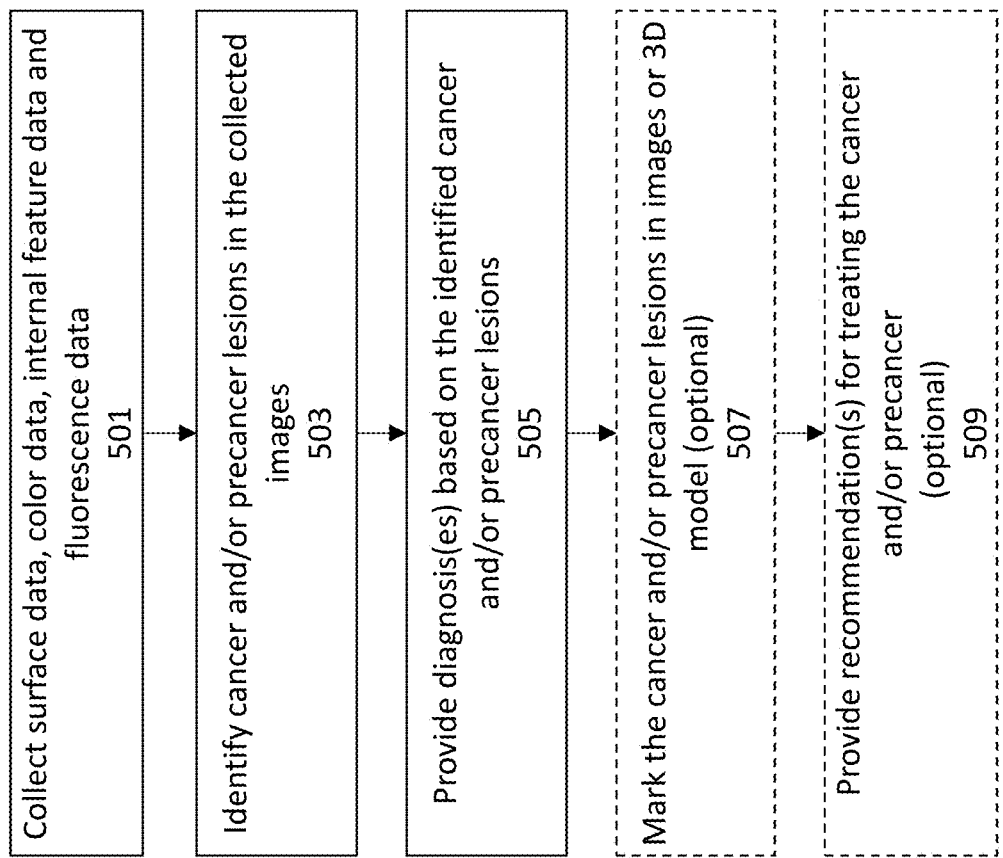
FIG. 5 is a flowchart illustrating an example method for identifying features indicative of oral cancer or precancer based on oral scans.

The intraoral scanning systems described herein can be used to detect provide a diagnosis of oral cancer and precancer based on the various image data collected using different scanning modalities. FIG. 5 is a flowchart illustrating an example method for identifying features indicative of oral cancer and precancer and providing one or more diagnoses based on oral scans. The intraoral scanner can be used to scan the patient's mouth to collect surface data, color data, internal feature data, and fluorescence data 501. The fluorescence data is associated with fluorescence imaging, which generally involves shining light on tissue and detecting naturally emitted light from biological structures, such as mitochondria and lysosomes (referred to as autofluorescence), or fluorescent dyes/proteins added to the tissue to visualize the tissue. Fluorescence imaging may be used as a technique to improve early identification of oral malignant and premalignant lesions based on the premise that normal healthy tissue can emit autofluorescence, while abnormal tissue can appear dark owing to decreased levels of autofluorescence. In some cases, the fluorescence imaging may also be used to detect the presence of plaque. The fluorescence imaging data can be collected concurrently with other image data using different imaging modalities (e.g., 3D (volumetric) imaging, color imaging, NIR imaging, and/or NIR spectroscopy) to provide a more comprehensive assessment of a patient's oral and dental health. For example, an accurate 3D model based on collecting data using the various scanning modalities can improve the detection and diagnosis of cancer and precancer. Additionally, comorbid, or aggravating conditions can be detected using the various scanning modalities, which fluorescence imaging alone may not detect. As described herein, the light source(s) for generating fluorescence may be the same light source(s) for providing the color and/or surface feature imaging, or may be separate light source(s).

Once collected, the data may be analyzed, and/or filtered (including subtracting, smoothing, etc.), or otherwise processes. In some cases, a 3D model rendering of the intraoral cavity (e.g., gums, teeth, jaw, etc.), or a portion of the intraoral cavity, using data from the different scanning modalities (e.g., surface, color, NIR and fluorescence). This can involve segmenting the images to distinguish anatomical surfaces structures and internal structures corresponding to the anatomical structures of the patient's mouth, including precancerous and/or cancerous lesions.

One or more features indicative of cancer and/or precancer in the collected scan images can be identified 503. This can involve using machine learning model (e.g., trained network) to identify and distinguish anatomical features (e.g., teeth, gums, connective tissue, bone etc.) and structures that are detected as likely being cancerous or precancerous lesions. As described above, the previously collected data used to train the machine learning model may include image data from previous 3D scans (e.g., including surface, color, NIR image data, and/or NIR spectroscopy data), X-ray images, periodontal charts (e.g., including probe depths), and/or visual inspection/tactile data from a dental professional.

In one example, the fluorescence imaging may detect a suspected cancerous or precancerous lesion in the patient's mouth based on fluorescence imaging pattern collected by the intraoral scanner. The color imaging data collected by the scanner can be used to detect the color of the tissue at the site suspected as being cancerous or precancerous, which can be used to verify or further support the identification based on the fluorescence imaging. In addition, the scanned images may be used to determine the size and shape of the suspected cancerous or precancerous lesion. Further, the NIR spectroscopy can be used to determine blood flow to the suspected site. Thus, the data provided by the various scanning modalities combined with the fluorescence imaging data can provide more comprehensive information compared to fluorescence imaging alone.

The intraoral scanning system can provide a possible diagnosis of cancer or precancer based on the identified features 505. The diagnosis may be based on a combination of features identified as being associated with cancer or precancer, as described above. The diagnosis may also involve determining a severity of the cancer or precancer based on the extent of the identified features. For example, those regions of tissue that include large lesions may be identified as being more severe cases compared to smaller lesions.

In some variations, the identified cancer or precancer lesions may be marked on the images or 3D model 507. For example, the features may be highlighted (e.g., using one or more colors) and/or labeled (e.g., using with symbols and/or lettering) on images or the 3D model as displayed on a display of the intraoral scanning system. In some variations, the system can be figured to provide one or more recommendations for treating the cancer or precancer based on the identified symptoms and proposed diagnosis(es) 509. In some case, the recommendation may include a recommendation for one or more follow up appointments to recheck the patient's oral health.

Multi-Modal Scanner with Fluorescence Imaging

As described herein, the intraoral scanners can include fluorescence imaging capability to detect indications of oral cancer or precancer (and plaque). The wavelengths of light emitted by the illumination source(s) in fluorescence imaging may vary depending on the target structure for imaging. The wavelengths of light used to illuminate the tissue to cause fluorescence of the tissue can be chosen to maximize detection efficiency of the different wavelengths of light. In some instances, the fluorescence illumination source(s) are configured to emit light in the blue to ultraviolet wavelengths of light (e.g., 380 nm to 495 nm (e.g., 400 nm)), which may be conducive to detecting cancerous and/or precancerous lesions. In some instances, the illumination source(s) are configured to emit red wavelengths of light (e.g., 625 nm to 740 nm), which may be conducive to detecting tooth lesions and/or dental plaque. In some examples, the illumination source(s) are configured to emit light both blue to ultraviolet wavelengths of light and red wavelengths of light for capturing tooth lesions, plaque and oral cancer/precancer.

The fluorescence imaging may be done concurrently with the scanning using other imaging modalities (e.g., volumetric, color, NIR), and can be done during a dental scan of a patient's dental arch, for example, during a routine dental exam. In some variations, the fluorescence imaging components may be integral part of an intraoral scanning system, where the fluorescence imaging components (e.g., light source, detector/sensor, optics, etc.) are enclosed within the body of the intraoral scanner along with the other imaging components of the scanner system. In some variations, the fluorescence imaging components correspond to one or more removable portions of the intraoral scanning system, such as a sleeve over the probe of the scanner. The optics of the 3D scanner used to capture the color intraoral 3D images can vary. In some variations, the optics may be confocal, involve stereo vision and/or structured light triangulation.

Figure 6:
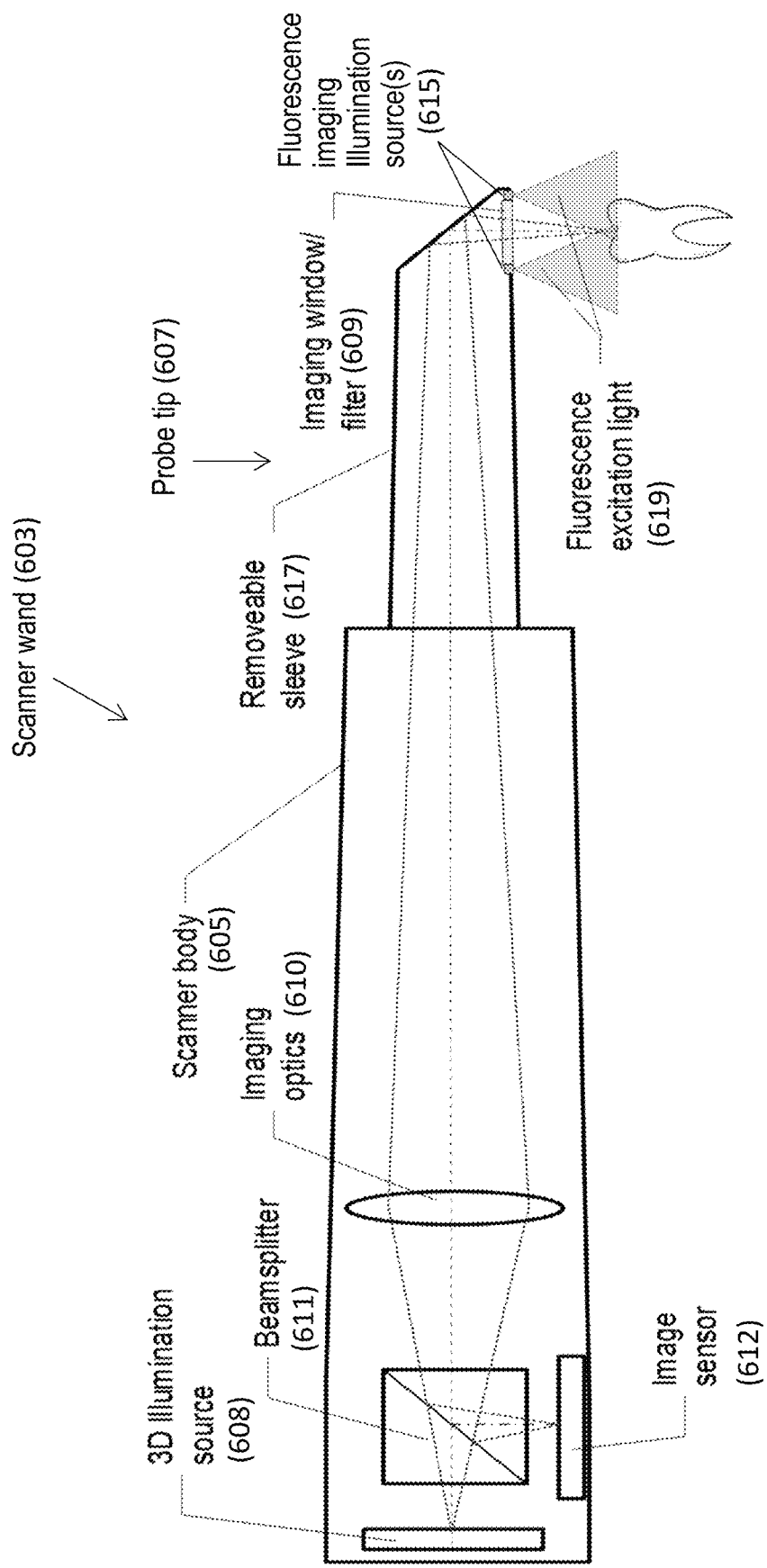
FIG. 6 illustrates an example fluorescence imaging component arrangement with a 3D confocal color intraoral scanner where at least some of the fluorescence imaging components are part of a removable sleeve for a wand of the intraoral scanner. The fluorescence-imaging component consist of short wavelength (e.g. 405 nm) LEDs and short wavelength cutoff filter window. The filter blocks the short wavelength light while allowing longer wavelength in the visible and NIR wavelength range. This arrangement can also be realized with rear mounted camera(s) and projector(s) doing triangulation 3D capture.

FIG. 6 illustrates an example of wand 603 of an intraoral scanning device having features to allow fluorescence imaging. The wand 603, which is configured for placement into a patient's mouth to collect scans, includes a scanner body 605 that is connected to a probe tip 607 (also referred to as the scanner head) at a distal end of the wand 603. The scanner body 605 can include an optical assembly for guiding transmitted light from a 3D illumination source 608 and/or received light from an imaging window 609 at a distal portion of the probe tip 607. The 3D illumination source 608 may include one or more light sources for capturing surface features and color images of the patient's mouth. The wand 603 may additionally include one or more IR (e.g., NIR) light sources for capturing IR (e.g., NIR) images of the patient's mouth. The optical assembly of the scanner body 605 can include one or more imaging optics 610 (e.g., lens(es) and/or mirror(s)), which direct at least a portion of the received light to one or more image sensors 610.

A distal end of the probe tip 607 includes one or more fluorescence imaging illumination sources 615 for shining fluorescence excitation light 619 on the patient's tissue inside the mouth. The excitation light 619 can cause living tissues and/or any fluorescent dyes/proteins to generate visible light via fluorescence, thereby generating fluorescence images. In this example, the probe tip 607 includes a removable sleeve 617 that includes the fluorescence imaging illumination source(s) 615 and an imaging window 609 that covers the probe tip 607. The removable sleeve 617 can optionally be removed from the probe tip 607 so that wand 603 can operate without fluorescence imaging. This removable sleeve configuration allows for flexibility according to the application needs with or without any particular light source suitable for the desired diagnostics feature. In other variations, the fluorescence imaging illumination source(s) 615 is located inside the probe tip 607 (e.g., not removeable from the probe tip). The fluorescence imaging illumination source(s) 615 can be located at a distal portion of the probe tip 607, and in some cases adjacent to (e.g., surrounding) the imaging window 609 so that the fluorescence excitation light 619 can be positioned near the object to be illuminated. The imaging window 609 may include one or more filters to attenuate the exciting light to reduce disturbance to the fluorescence imaging (e.g., reduce noise). The optical assembly (imaging optics 610 and beam splitter 611) can focus and guide the fluoresced light (along with reflected light associated with the surface features, color images and penetration images) to the one or more image sensors 612, which can be configured to detect the fluoresced light as well reflected light associated with the surface features, color images and penetration images. In some cases, the processing system can combine the detected fluorescence light signals (including any fluorescence images of cancerous/ precancerous lesion) along with detected visible light and/or IR light signals to form a 3D model of the patient's the gums and teeth.

Figure 7:
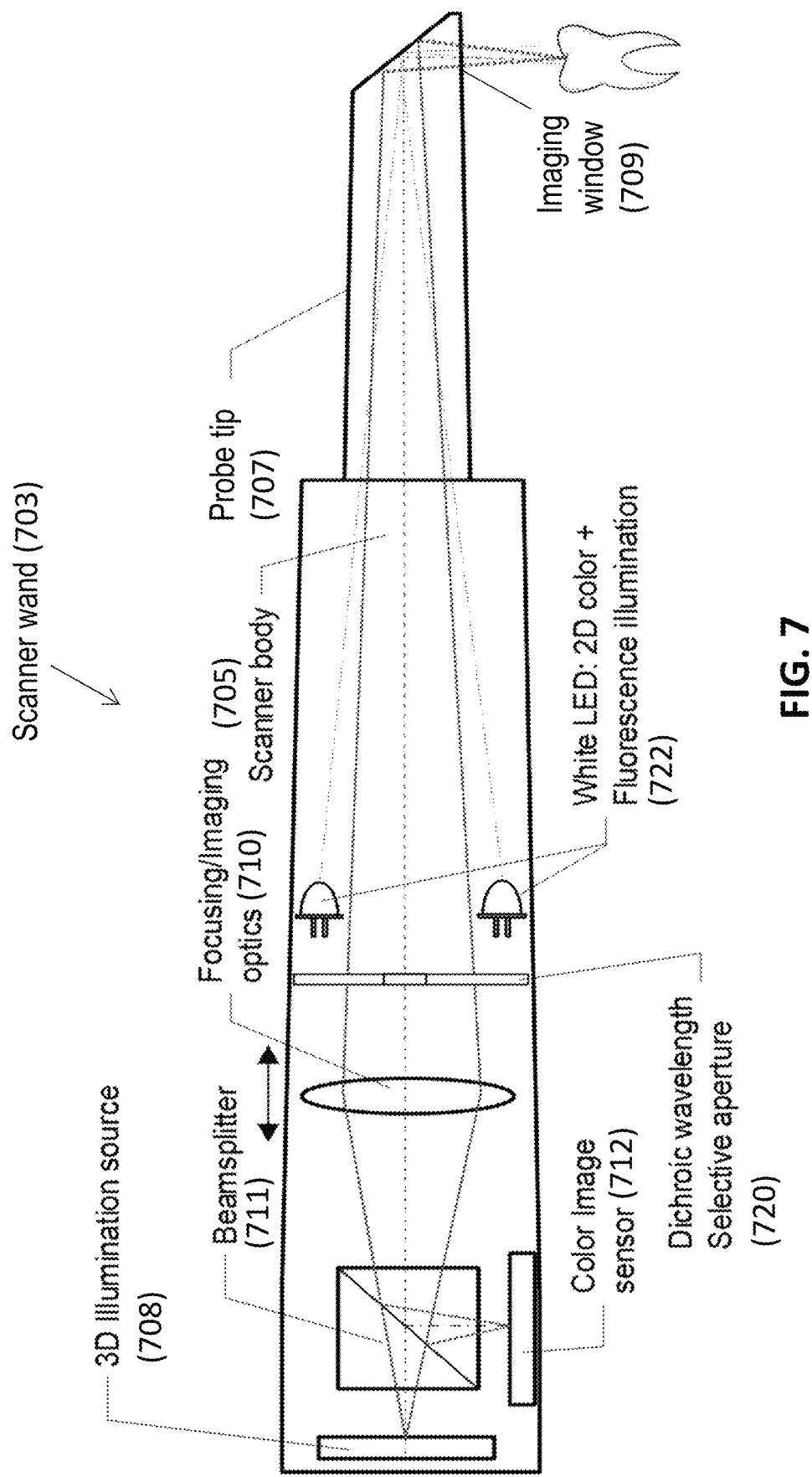
FIG. 7 illustrate another example fluorescence imaging component arrangement with a 3D color confocal intraoral scanner where at least some of the fluorescence imaging components are within a scanner body of the intraoral scanner wand. The fluorescence imaging light source consists of white light LEDs in which the short wavelength blue light (e.g. 450 nm) is embedded in the white LED emission spectra. In this case, no filter is used, and the fluorescence imaging is extracted from the 2D color images.

FIG. 7 illustrates an example scanner wand 703 having a different fluorescence imaging component arrangement. In this example, the scanner body 405 includes one or more light sources 722 that are configured to generate white light (e.g., white LED), which can be used to illuminate objects for the visible light (color) imaging and cause fluorescence for fluorescence imaging. In some variations, the white LED is configured to generate a strong 450 nm signal of the white light that can serve as a major contributor to fluorescence excitation. White light from the light source(s) 722 can be directed from the scanner body 705, through the probe tip 707 and out the imaging window 709. When the white light shines on the gums and teeth of the patient (during the scanning procedure), the gums and teeth can reflect visible light for color imaging and also cause living tissues to generate visible light via fluorescence for the fluorescence imaging. The reflected light and fluoresced light can enter the imaging window and be directed through the probe tip 707 and back within the scanner body 705. In addition, the 3D illumination source 708 can generate a spectral range of light for detection of surface features. One or more dichroic wavelength selective apertures/filters 720 can allow selected wavelengths of the fluoresced light and/or reflected light to pass in order to reduce noise. The focusing/imaging optics 710 and beam splitter(s) 711 can direct the reflected light and fluoresced light to the image sensor(s) 712. In some variations, the image sensor(s) includes a color filter (e.g., Bayer filter) that can be controlled (e.g., via computer with machine learning) to separate the non-fluorescence light, 3D surface feature signals and color signals.

Figure 8:
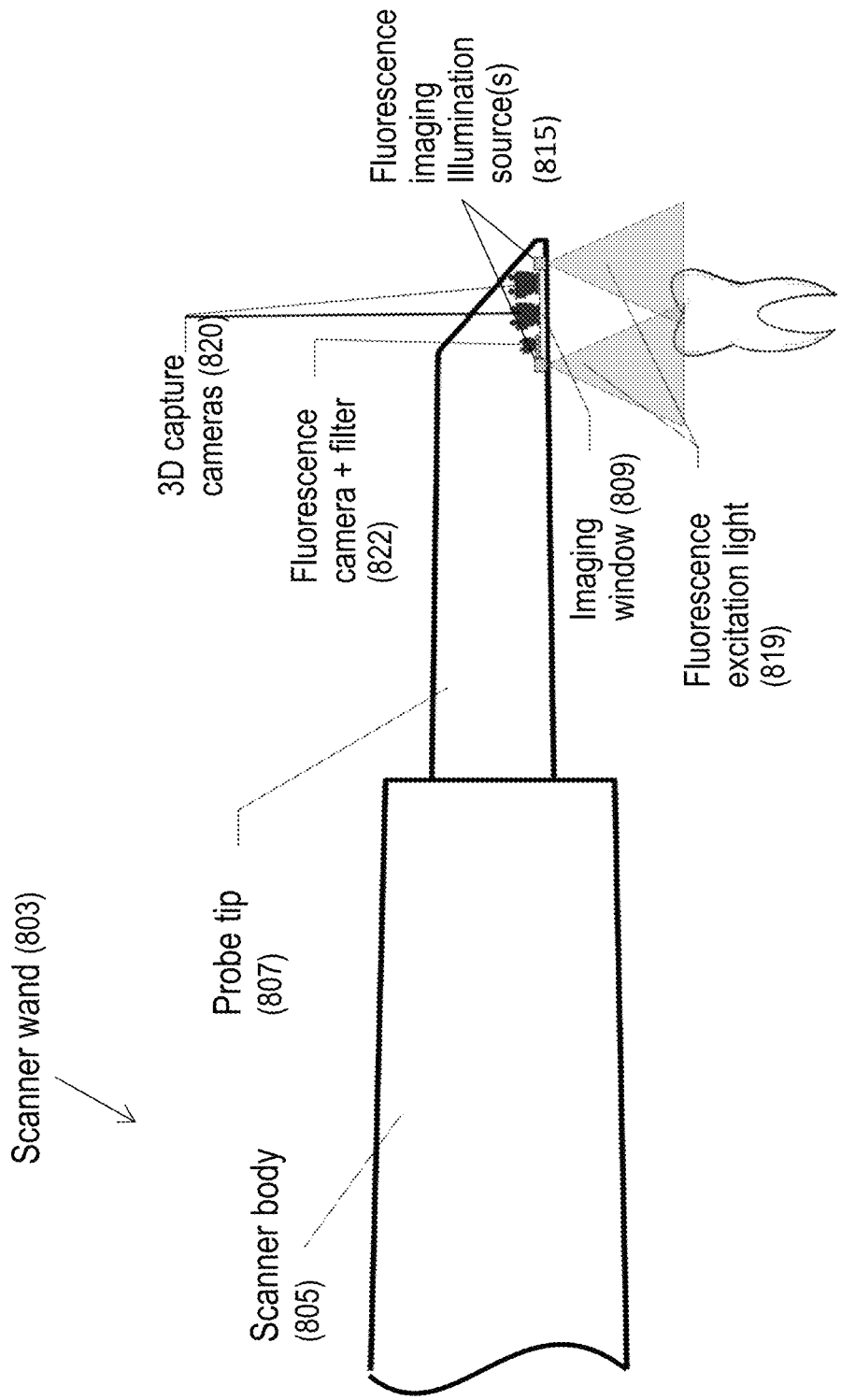
FIG. 8 illustrate a further example fluorescence imaging component arrangement within a tip mounted camera(s) and projector(s) 3D triangulation color intraoral scanner where at least some of the fluorescence imaging components are within a probe tip of the intraoral scanner wand. The fluorescence imaging components consist of short wavelength (e.g. 405 nm) LEDs and short wavelength cutoff filter window. The filter blocks the short wavelength light while allowing longer wavelength in the visible and NIR wavelength range.

FIG. 8 illustrates an example scanner wand 803 having a fluorescence imaging component arrangement like the wand 803 of FIG. 3 except with a different sensor/detector arrangement. In this example, the probe tip 807 includes one or more fluorescence imaging illumination sources 815 configured to generate fluorescence excitation light 819 onto the illumination target. The fluorescence imaging illumination source(s) 815 may include short wavelength LEDs located at the distal end of the probe tip 806 facing the illumination target. The probe tip 807 can also include one or more fluorescence cameras 822 for capturing fluoresced light. The fluorescence camera(s) 822 may be equipped with a fluorescence exciting light attenuation filter suitable for the type of lesion to be captured. One or more 3D capture cameras 820 can be configured to capture reflected light for 3D surface, color and penetration images. In some variations, the fluorescence camera(s) and filter(s) 822 and/or 3D capture camera(s) 820 is miniature in size and face the illumination target (through the imaging window 809). This configuration allows for capture of 3D images (and color and penetration image) as well as fluorescence images concurrently or within a proximal time frame. The proximity of the respective data captures may be used for straightforward combination of the fluorescence images with other captured imaged for more accuracy in generating the images or 3D model. Note that the scanner body 805 can include one or more illumination sources for the surface feature, color and/or NIR images but are not shown for simplicity.

Figure 9:
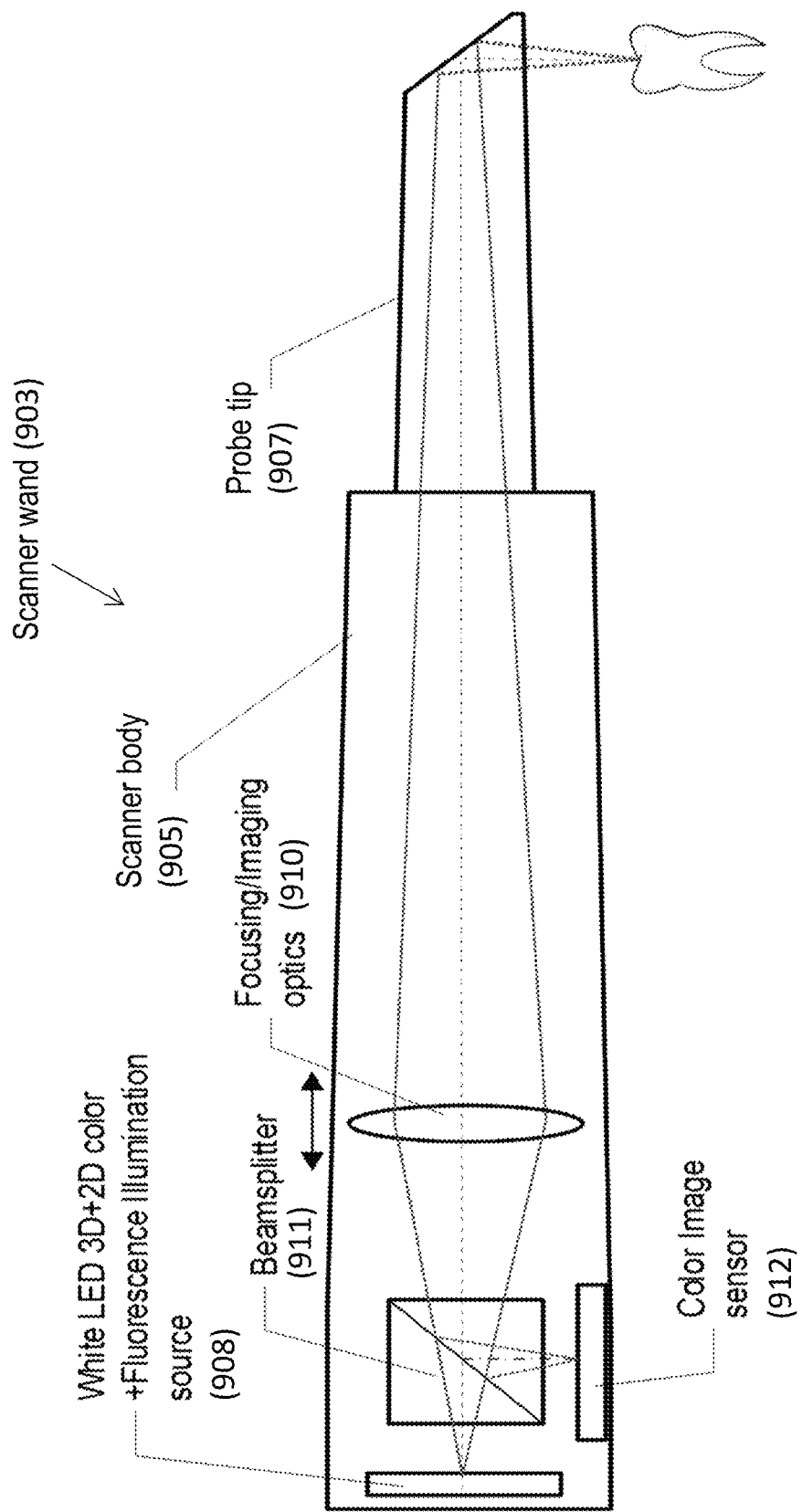
FIG. 9 illustrate another example fluorescence imaging component arrangement within the scanner body of the intraoral scanner wand wherein a confocal 3D color intraoral scanner utilizes a white LED 3D light source (908) having a strong short wavelength spectral component (e.g. 450nm) for fluorescence imaging along with the white light used for 3D imaging and 2D color imaging.

FIG. 9 illustrates an example scanner wand 903 having a fluorescence imaging component arrangement with the fluorescence illumination source(s) located in the scanner body 905 instead of the probe tip 907. In this example, the scanner body 905 includes a white light source 908 (e.g., LED), which can be used for 3D surface feature imaging, 2D color imaging, and as the fluorescence imaging excitation light source. For example, the white light source 608 (e.g., LED) can be configured to generate a strong 450 nm signal that can serve as the fluorescence excitation light. The internal optical components (e.g., focusing/imaging optics 910 and beam splitter(s) 611) can focus and guide the outgoing and incoming light. Incoming reflected light and fluoresced light can be directed to one or more sensors 912, which can include one or more color image sensors. The sensor(s) 912 may serve as a selective fluorescent image sensor, for example, using a built-in Bayer color filter and an intelligent (machine learning) algorithm behind it that digitally separates the non-fluorescent and the 3D surface imaging and the 2D color signals.

Figure 10:
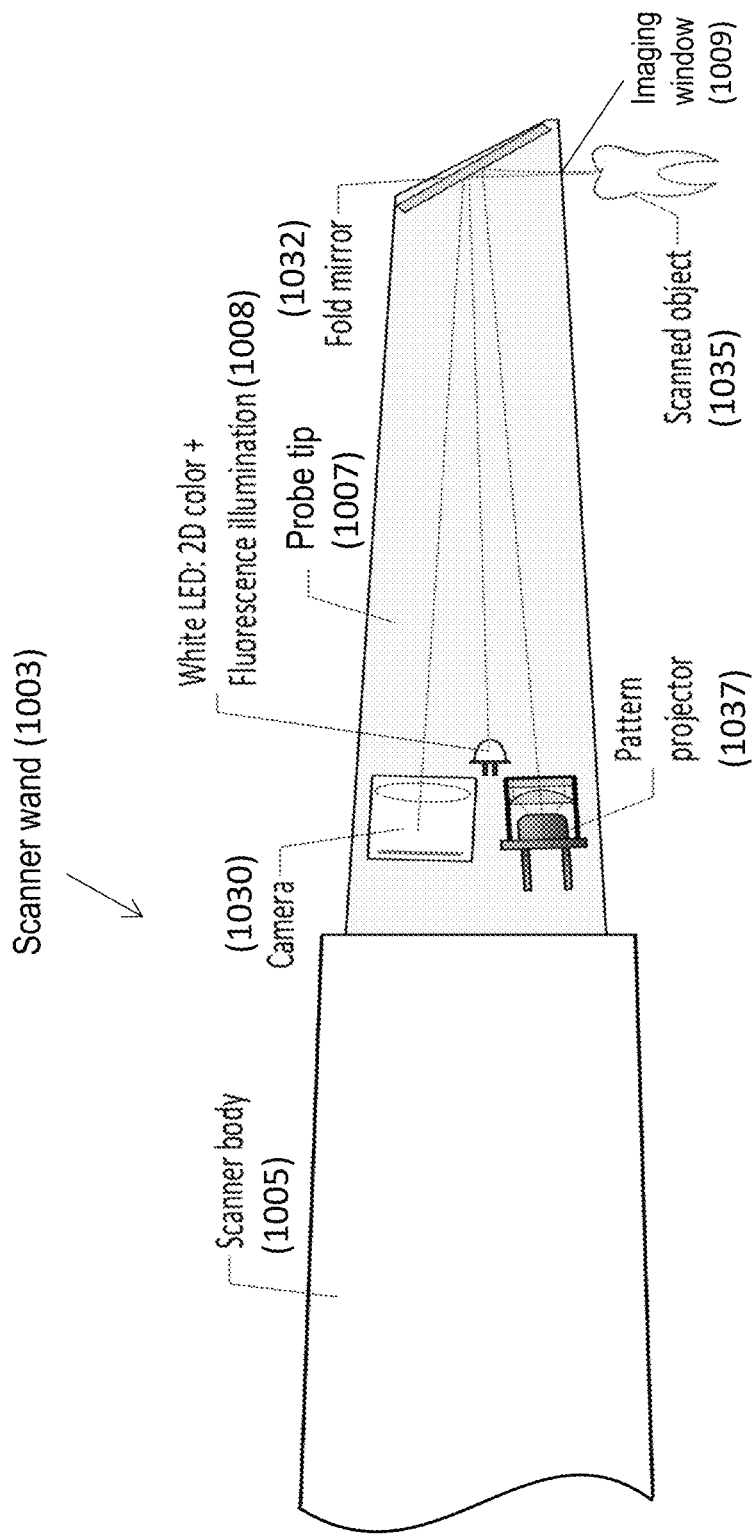
FIG. 10 illustrate a further example fluorescence imaging component arrangement with a rear mounted camera(s) and projector(s) triangulation 3D color intraoral scanner wherein a white light LED (1008) is added to the triangulation setup to facilitate fluorescence and 2D color imaging.

FIG. 10 illustrates an example scanner wand 1003 having one or more cameras 1030 and pattern projector 1037, which may be in the probe tip 1007. This arrangement may be suitable for rear-located structured light scanner. One or more white light sources 1008 (e.g., LED) can generated white light for color imaging and can generate a strong 450 nm signal that can serve as the fluorescence excitation light. The wand 1003 can include one or more mage cameras 1030 that can serve as a selective fluorescent image sensor, for example, using a built-in Bayer color filter and an intelligent (machine learning) algorithm behind it that digitally separates the non-fluorescent and the 3D surface imaging and the 2D color signals. The pattern projector 1037 can be configured to project one or more patterns for structured machine vision inspection. The distal end of the probe tip 1007 can include a mirror 1032 for directing incoming and outgoing light through the imaging window 1009 (as with any of the examples shown in FIGS. 6-9).

Computing System

Figure 15:
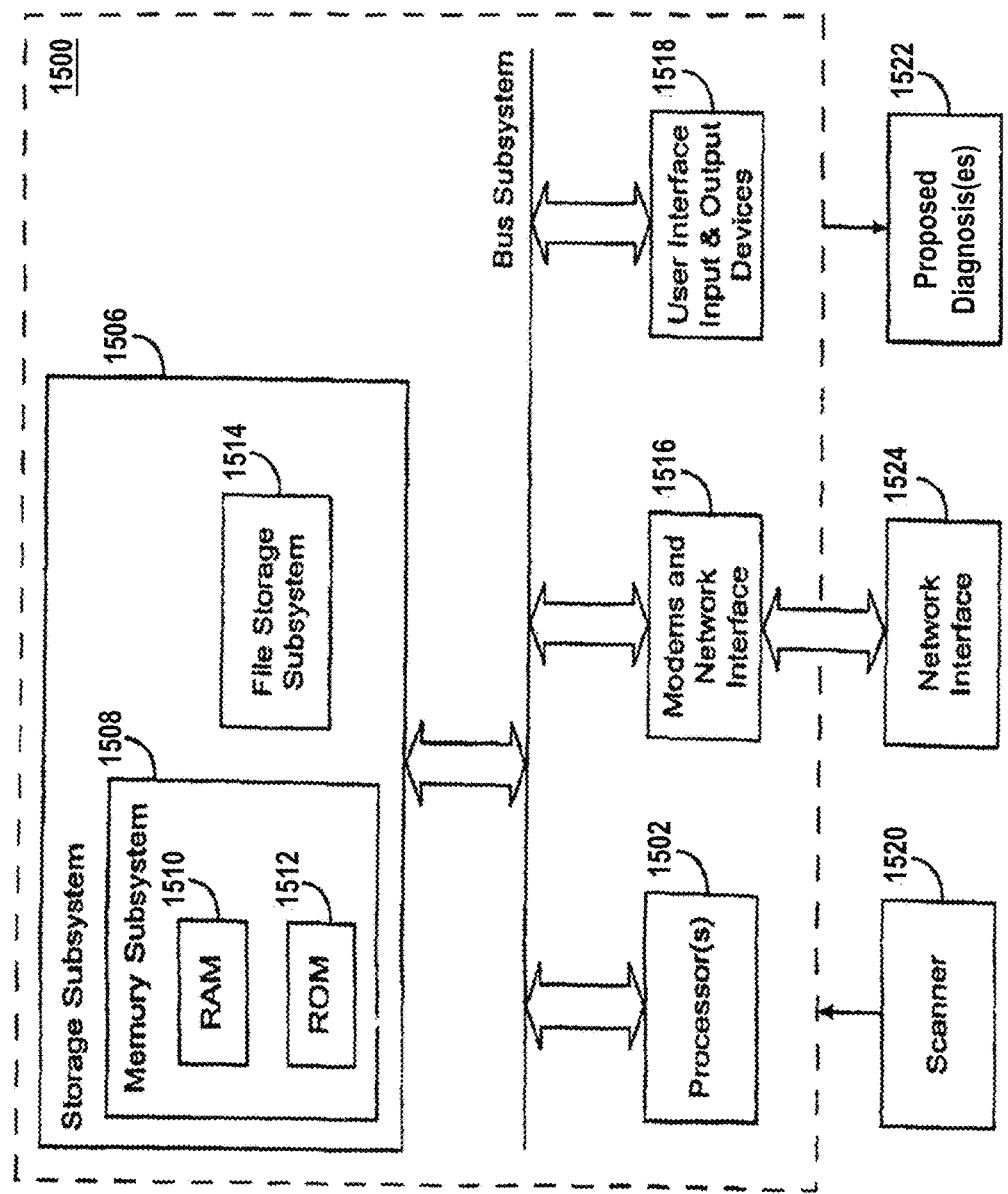
FIG. 15 is a simplified block diagram of a computing system that may perform the methods described herein.

The methods described herein may be performed by an apparatus, such as a computing system, which may include hardware, software, and/or firmware for performing many of these steps described above. For example, FIG. 15 is a simplified block diagram of a computing system 1500. Computing system 1500 typically includes at least one processor 1502 which communicates with a number of peripheral devices over bus subsystem 1504. These peripheral devices typically include a storage subsystem 1506 (memory subsystem 1508 and file storage subsystem 1514), a set of user interface input and output devices 1518, and an interface to outside networks 1516, including the public switched telephone network. This interface is shown schematically as "Modems and Network Interface" block 1516 and is coupled to corresponding interface devices in other computing systems over communication network interface 1524. Computing system 1500 may include a terminal or a low-end personal computer or a high-end personal computer, workstation, or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 1506 maintains the basic programming and data constructs that provide the functionality of the present invention. The software modules discussed above are typically stored in storage subsystem 1156. Storage subsystem 1106 typically comprises memory subsystem 1508 and file storage subsystem 1514.

Memory subsystem 1508 typically includes a number of memories including a main random-access memory (RAM) 1510 for storage of instructions and data during program execution and a read only memory (ROM) 1512 in which fixed instructions are stored. In the case of Macintosh-compatible personal computers the ROM would include portions of the operating system; in the case of IBM-compatible personal computers, this would include the BIOS (basic input/output system).

File storage subsystem 1514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 1504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 1520 is responsible for scanning casts of the patient's teeth obtained either from the patient or from an orthodontist and providing the scanned digital data set information to computing system 1500 for further processing. In a distributed environment, scanner 1520 may be located at a remote location and communicate scanned digital data set information to computing system 1500 over network interface 1524. The system 1500 can be used to provide one more proposed diagnoses 1522 for one or more oral conditions/diseases based on processing of data set information acquired from computing system 1500.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high-level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, the method comprising:
receiving or accessing scan data collected from an oral scan of a subject's oral cavity, including a dental arch, the scan data including at least three of: three-dimensional (3D) surface data, color image data, near-infrared (NIR) data, and fluorescence imaging data;

identifying one or more features indicative of gingival inflammation in the scan data using a trained machine learning model, wherein the trained machine learning model is trained on image data including at least three of: previous 3D surface data, previous color image data, previous near-infrared (NIR) data, and previous fluorescence imaging data, wherein the data used to train the trained machine learning model is filtered based on a threshold angle between images of the color image data and a threshold distance between the images of the color image data; and outputting an indication of gingival inflammation based on the one or more features indicative of gingival inflammation.

2. The method of claim 1, wherein outputting comprises marking the one or more features indicative of gingival inflammation on images or a 3D model of the subject's dental arch on a display.

3. The method of claim 2, wherein marking the one or more features indicative of gingival inflammation includes highlighting or labeling the one or more features indicative of gingival inflammation.

4. The method of claim 1, wherein the one or more features indicative of gingival inflammation include one or more measurements of a cementoenamel junction (CEJ) that are sufficiently high to be associated with gum recession.

5. The method of claim 1 wherein the one or more features indicative of gingival inflammation include one or more measurements of the subject's gums that that are sufficiently red to be associated with gingival inflammation.

6. The method of claim 1, wherein the one or more features indicative of gingival inflammation include one or more measurements of dental pocket depth that are sufficiently high to be associated with gum recession.

7. The method of claim 1, wherein the one or more features indicative of gingival inflammation include one or more measurements of blood serum concentration sufficiently high to be associated with gingival inflammation.

8. The method of claim 1, wherein the trained machine learning model is further trained based on X-ray image data, periodontal chart data and visual inspection/tactile data.

9. The method of claim 1, wherein the trained machine learning model is further trained based on NIR spectroscopy data.

10. The method of claim 1, further comprising monitoring changes to the one or more features indicative of gingival inflammation over time to determine improvement or worsening of symptoms of gingival inflammation.

11. The method of claim 10, further comprising updating a diagnosis of gingival inflammation based on the changes to the one or more features indicative of gingival inflammation.

12. The method of claim 10, further comprising providing a time lapse video showing the changes to the one or more features indicative of gingival inflammation.

13. A method of diagnosing oral cancer or precancer in a subject, the method comprising:

capturing scan data using an intraoral scanner on the subject's oral cavity, wherein the scan data includes three-dimensional (3D) surface data, color image data, near-infrared (NIR) data, and fluorescence imaging data;

identifying one or more cancer or precancer lesions in the 3D surface data of the scan data using a trained machine learning model, wherein the trained machine learning model is trained on image data including includes previous 3D surface data, previous color image data, previous near-infrared (NIR) data, and previous fluorescence imaging data, wherein the data used to train the trained machine learning model is filtered based on a threshold angle between images of the color image data and a threshold distance between the images of the color image data; and outputting an indication of oral cancer or precancer based on the identified one or more cancer or precancer lesions.

14. The method of claim 13, wherein capturing the scan data comprises concurringly collecting the 3D surface data, color image data, near-infrared (NIR) data, and fluorescence imaging data.

15. The method of claim 13, further comprising determining a size and shape of the one or more cancer or precancer lesions.

16. The method of claim 13, wherein the trained machine learning model is further trained based on X-ray image data, periodontal chart data and visual inspection/tactile data.

17. The method of claim 13, wherein the trained machine learning model is further trained based on NIR spectroscopy data.

18. The method of claim 13, wherein the trained machine learning model is further trained based on fluorescence imaging data collected from previous scans of the subject's oral cavity.

19. A system, the system comprising:

one or more processors;

a memory, accessible by the one or more processors and storing computer-program instructions, that, when executed by the one or more processors, perform a computer-implemented method comprising:

receiving or accessing scan data collected from an oral scan of a subject's oral cavity, the scan data including at least three of: three-dimensional (3D) surface data, color image data, near-infrared (NIR) data, and fluorescence imaging data;

identifying one or more features indicative of gingival inflammation in the scan data using a trained machine learning model, wherein the trained machine learning model is trained on image data including at least three of: previous 3D surface data, previous color image data, previous near-infrared (NIR) data, and previous fluorescence imaging data, wherein the data used to train the trained machine learning model is filtered based on a threshold angle between images of the color image data and a threshold distance between the images of the color image data; and outputting an indication of gingival inflammation gingival inflammation based on the one or more features indicative of gingival inflammation.

20. The system of claim 19, further comprising a hand-held wand having at least one image sensor and a plurality of light sources, wherein the plurality of light sources is configured to emit light at a visible light range, a florescent light range, and an infrared light range.

21. The system of claim 19, wherein the computer-implemented method further comprises:

capturing data of at least a portion of the subject's teeth as an intraoral scanner is moved over the subject's teeth, wherein the captured data includes 3D surface data, color image data, near-infrared (NIR) data, and fluorescence imaging data.

\* \* \* \* \*